US012636291B2

(12) United States Patent
Prevot et al.

(10) Patent No.: US 12,636,291 B2
(45) Date of Patent: May 26, 2026

(54) COMPOSITIONS AND METHODS RELATING TO USE OF AGONISTS OF ALPHA5-CONTAINING GABAA RECEPTORS

(71) Applicant: Centre for Addiction and Mental Health, Toronto (CA)

(72) Inventors: Thomas D. Prevot, Toronto (CA); Mounira Banasr, Toronto (CA); Etienne Sibille, Toronto (CA)

(73) Assignee: Centre for Addiction and Mental Health, Toronto (CA)

( * ) Notice: Subject to any disclaimer, the term of this patent is extended or adjusted under 35 U.S.C. 154(b) by 1196 days.

(21) Appl. No.: 17/310,549

(22) PCT Filed: Feb. 12, 2020

(86) PCT No.: PCT/IB2020/051149
§ 371 (c)(1),
(2) Date: Aug. 10, 2021

(87) PCT Pub. No.: WO2020/165802
PCT Pub. Date: Aug. 20, 2020

(65) Prior Publication Data

US 2022/0105106 A1 Apr. 7, 2022

Related U.S. Application Data

(60) Provisional application No. 62/924,378, filed on Oct. 22, 2019, provisional application No. 62/805,009, filed on Feb. 13, 2019.

(51) Int. Cl.
*A61K 31/5517* (2006.01)
*A61P 25/28* (2006.01)

(52) U.S. Cl.
CPC .......... *A61K 31/5517* (2013.01); *A61P 25/28* (2018.01)

(58) Field of Classification Search
CPC ............................ A61K 31/5518; A61P 25/18
See application file for complete search history.

(56) References Cited

U.S. PATENT DOCUMENTS

| | | | | |
|---|---|---|---|---|
| 7,618,958 | B2 | 11/2009 | Cook et al. | |
| 8,835,424 | B2 | 9/2014 | Cook et al. | |
| 10,906,909 | B2 * | 2/2021 | Cook | A61P 25/00 |
| 11,753,412 | B2 * | 9/2023 | Cook | A61P 25/28 514/364 |

FOREIGN PATENT DOCUMENTS

| | | | | |
|---|---|---|---|---|
| WO | 2007053596 | A1 | 5/2007 | |
| WO | WO-2010051503 | A1 * | 5/2010 | A61P 43/00 |
| WO | 2012068149 | A1 | 5/2012 | |
| WO | 2015095783 | A1 | 6/2015 | |
| WO | WO-2016205739 | A1 * | 12/2016 | A61K 31/13 |
| WO | WO-2017161370 | A1 * | 9/2017 | A61P 25/28 |

OTHER PUBLICATIONS

Schaeffer (Clinics vol. 55 pp. 45-54 published 2011) (Year: 2011).*
American Psychological Association (2011). (Year: 2011).*
Lin (Frontiers in Psychiatry vol. 8 published Nov. 21, 2017). (Year: 2017).*
International Search Report and Written Opinion of the International Searching Authority mailed on May 6, 2020 for International Application No. PCT/IB2020/051149, filed Feb. 12, 2020, 9 pages.
Prevot, T.D. et al, Novel Benzodiazepine-Like Ligands with Various Anxiolytic, Antidepressant, or Pro-Cognitive Profiles, Molecular Neuropsychiatry, (Jan. 23, 2019), 5:84-97.
Kennedy and O'Riordan, "Prescribing benzodiazepines in general practice," British Journal of General Practice, vol. 69: 152-153 (Mar. 2019).
Barker et al., "Persistence of cognitive effects after withdrawal from long-term benzodiazepine use: a meta-analysis," Archives of Clinical Neuropsychology, vol. 19: 437-454 (2004).
Fujita et al., "Changes of benzodiazepine receptors during chronic benzodiazepine administration in humans," European Journal of Pharmacology, vol. 368: 161-172 (1999).
Nicholson et al., "Diazepam-induced loss of inhibitory synapses mediated by PLCδ/$Ca^2$+/calcineurin signalling downstream of GABAA receptors," Molecular Psychiatry, vol. 23: 1851-1867 (2018).
Stevens et al., "Benzodiazepines in Clinical Practice: Consideration of Their Long-Term Use and Alternative Agents," Journal of Clinical Psychiatry, vol. 66 [supp 2]: 21-27 (2005).

* cited by examiner

*Primary Examiner* — George W Kosturko
(74) *Attorney, Agent, or Firm* — KDW Firm PLLC

(57) ABSTRACT

The invention provides methods and related compositions for preventing neurocognitive decline associated with chronic stress, age, and neurodegenerative diseases. The methods described here are based upon the use of alpha5-GABAA receptor agonists to slow or prevent deleterious morphological changes in dendrites of the hippocampus and prefrontal cortex, which eventually manifest in functional decline and the neurocognitive deficits.

15 Claims, 32 Drawing Sheets

COMPOSITIONS AND METHODS RELATING TO USE OF AGONISTS OF ALPHA5-CONTAINING GABAA RECEPTORS

CROSS-REFERENCE TO RELATED APPLICATIONS

This application is a national stage entry, filed under 35 U.S.C. § 371, of International Application No. PCT/IB2020/051149, filed on Feb. 12, 2020, which claims the benefit of U.S. Pat. No. 62/924,378, filed on Oct. 22, 2019 and U.S. Provisional Application No. 62/805,009, filed on Feb. 13, 2019, the entire contents of which is hereby incorporated herein by reference in its entirety and for all purposes.

FIELD OF THE DISCLOSURE

The present invention relates to new uses of compounds that modulate alpha5-containing GABAA receptors, and related compositions and methods.

BACKGROUND OF THE DISCLOSURE

Advances in science and medicine have increased people's average lifespan over the past 100 years, with a worldwide life expectancy expected to reach 80 years in 2050 (WHO). More people are living longer and also experiencing age-related disabilities that were not common few decades ago. This extended aging period, associated with biological changes due to normal aging, facilitates the onset of neurodegenerative diseases such as Alzheimer's disease.

Alzheimer's disease (AD) was first characterized by the accumulation of β-amyloid plaques and the extensive production of the Tau-protein in the brain. These changes are associated with reduced brain cell structure (i.e. reduced dendrites and spines) and eventually cell loss. These latter changes occur naturally during normal aging and are an immediate cause of cognitive decline and memory dysfunction in both normal aging and AD. Crews L and Masliah E (2010) "Molecular mechanisms of neurodegeneration in Alzheimer's disease" *Human Molecular Genetics* DOI10.1093. Notably these latter cellular changes occur on an accelerated trajectory in AD and are thought to contribute and worsen the β-amyloid plaques and Tau-protein pathologies and associated cognitive symptoms (Morrison J H, Baxter M G (2012): The ageing cortical synapse: hallmarks and implications for cognitive decline. *Nature reviews Neuroscience.* 13:240-250). Together, this demonstrates an age-by-AD pathology interaction, and suggests that slowing down the cellular changes or reduced neuroplasticity associated with normal aging will reduce the risk or delay the onset of symptoms of Alzheimer's disease and other age-related neurodegenerative disorders.

To date, a large number of different mechanisms have been proposed to cause dendritic spine dysfunction and loss in AD. For instance, amyloid beta fibrils, diffusible oligomers, or the intracellular accumulation of amyloid beta, have been found to alter the function and structure of dendritic spines by distinct mechanisms. Furthermore, Tau hyperphosphorylation and microglia activation, which are thought to be consequences of amyloidosis in AD, may also contribute to spine loss (Dorostkar et al. (2015): Analyzing dendritic spine pathology in Alzheimer's disease: problems and opportunities. *Acta neuropathologica.* 130:1-19). Yet, despite promising leads, there has been no successful translation into therapeutic approaches for AD, because of a lack of efficacy in affecting the symptoms or in stopping or delaying the onset or the underlying pathologies. Facing the ineffectiveness of pharmacological treatment being developed, the pharmaceutical industry came up with 2 options: 1) explore novel therapeutic avenues based on other underlying mechanisms and 2) act prior to the onset of the symptoms to slow down the disease (Prevention, Prophylaxis)(Reiman et al. (2011): Alzheimer's Prevention Initiative: a plan to accelerate the evaluation of presymptomatic treatments. *Journal of Alzheimer's disease: JAD.* 26 Suppl 3:321-329). The prophylaxis approach, if effective, would dramatically reduce the burden of the illness since delaying the onset of symptoms by only 5 years in elderly subjects would significantly lower disease prevalence as well as its costs (Zissimopoulos et al. (2014): The Value of Delaying Alzheimer's Disease Onset. *Forum Health Econ Policy.* 18:25-39). Hence, delaying onset of Alzheimer's Disease has significant economic and longevity benefits.

To prevent the onset of disease, limiting the functional and morphological loss of neuronal cells has been proposed as a potential therapeutic avenue. This could include neuronal functional or morphological changes due to normal aging, to Alzheimer's disease or due to the interaction of these two factors. To date, only a few pharmaceutical agents have been suggested to act to prevent the early cellular changes in the brain that occur in aging and neurodegenerative diseases and which underpin the functional and morphological loss of neuronal cells, such as the decrease in the arborization and complexity of dendritic trees. Riluzole, a glutamate modulator that decreases glutamate release by increasing its reuptake by astrocytes, reversed cognitive deficit related to normal aging in rats, by increasing the clustering of thin spines in the CA1 of the dorsal hippocampus (Pereira et al. (2014): Glutamatergic regulation prevents hippocampal-dependent age-related cognitive decline through dendritic spine clustering. *Proceedings of the National Academy of Sciences of the United States of America.* 111:18733-18738). The new fast acting antidepressants ketamine or scopolamine were also shown to rapidly increase spine synapse number in the PFC of rodents and to reverse the effects of chronic stress (Duman C H, Duman R S (2015): Spine synapse remodeling in the pathophysiology and treatment of depression. *Neuroscience letters.* 601:20-29).

Recent studies have shown that reductions in GABA levels may underlie the behavioral and psychological symptoms of both normal ageing and AD and may specifically contribute to cognitive impairment (Solas M et al. (2015): Treatment Options in Alzheimer s Disease: The GABA Story. *Current pharmaceutical design.* 21:4960-4971). GABA is the main inhibitor in the central nervous system and GABA signals through different receptor subtypes, mainly classified under 2 families, GABA(A) and GABA(B) receptors. Among the different subunits composing the GABA(A) receptors, the alpha5-subunit shows important decreases in expression correlated with aging and AD severity (Rissman et al. (2003): Biochemical analysis of GABA (A) receptor subunits alpha 1, alpha 5, beta 1, beta 2 in the hippocampus of patients with Alzheimer's disease neuropathology. *Neuroscience.* 120:695-704), and is particularly expressed in brain regions highly involved in cognitive processes such as hippocampus and the prefrontal cortex (Gill K M, Grace A A (2014): The role of alpha5 GABAA receptor agonists in the treatment of cognitive deficits in schizophrenia. *Current pharmaceutical design.* 20:5069-5076; Behlke et al. (2016): A Pharmacogenetic 'Restriction-of-Function' Approach Reveals Evidence for Anxiolytic- Like Actions Mediated by alpha5-Containing GABAA Receptors in Mice. *Neuropsychopharmacology: official publication of the American College of Neuropsychopharmacology.* 41:2492-2501). Selective activity at α5-GABAA-receptors has also been suggested to play a role in alleviating "behavioral emotionality" (anxiety and depressive-like behaviors) in mouse models or alleviating cognitive dysfunction in mouse models of schizophrenia and in old animals (Gill et al. (2011): A Novel α5GABA(A)R-Positive Allosteric Modulator Reverses Hyperactivation of the Dopamine System in the MAM Model of Schizophrenia. *Neuropsychopharmacology.* 36:1903-1911; Koh et al. (2013): Selective GABA(A) alpha5 positive allosteric modulators improve cognitive function in aged rats with memory impairment. *Neuropharmacology.* 64:145-152; Prevot et al. (2018): Novel benzodiazepine-like ligands with various anxiolytic, antidepressant or pro-cognitive profiles. *Molecular neuropsychiatry*).

To date, no drug acting directly on the GABAergic system has shown an effect on the early cellular changes such as neuronal dendrite and spine formation, which precede the development of cognitive impairment and neurocognitive decline that manifest with age, chronic stress, and neurological disorders such as Alzheimer's disease.

New therapeutic approaches are needed that specifically target and slow or prevent the underlying cellular changes that contribute to the functional alterations that eventually manifest as cognitive impairment and neurocognitive decline. Ideally, approaches are needed that act prior to the onset of the symptoms and prevent or slow down the underlying cellular changes that contribute to neuronal dysfunction. The present invention addresses this need.

SUMMARY OF THE DISCLOSURE

The present invention is based, in part, on the discovery that an agonist of alpha5-containing GABAA receptors acts to prevent early cellular changes in pyramidal cells, including decreases in dendritic length, number of spines, and spine density. These changes are measures of pyramidal cell dendritic arborization and the complexity of dendritic trees, which are the morphological features of pyramidal cells that are reduced in normal aging and in neurodegenerative diseases and disorders, such as Alzheimer's disease, and which reduction or loss contributes to the functional alterations that eventually manifest as cognitive impairment and neurocognitive decline. The disclosure also provides evidence that the prevention of these morphological changes in pyramidal cells by chronic administration of an alpha5-GABAA receptor agonist is effective to prevent cognitive impairment associated with aging in a mouse model system.

Accordingly, the disclosure provides methods for preventing or delaying the onset of one or more symptoms of cognitive impairment or neurocognitive decline in a subject in need thereof, the method comprising administering to the subject a pharmaceutical composition comprising an alpha5-GABAA receptor agonist. The disclosure also provides methods for preventing or delaying the onset of age-related morphological changes in neuronal cells, especially pyramidal cells, that contribute to the functional alterations that eventually manifest as symptoms of cognitive impairment and neurocognitive decline. Further, the disclosure provides methods for stimulating neurogenesis in a subject in need thereof, the methods comprising administering to the subject a pharmaceutical composition comprising an alpha5-GABAA receptor agonist.

In embodiments, the subject in need is asymptomatic prior to administering the alpha5-GABAA receptor agonist.

In embodiments, the subject in need is one who is at risk of developing a neurodegenerative disease or disorder. In embodiments, the neurodegenerative disease or disorder is selected from Alzheimer's disease, mild cognitive impairment, amyotrophic lateral sclerosis, multiple sclerosis, Parkinson's disease, Huntington's disease, and frontotemporal degeneration. In embodiments, the neurodegenerative disease or disorder is Alzheimer's disease. In embodiments, the subject has a genetic predisposition to the neurodegenerative disease or disorder. In embodiments, the method further comprises a step of assaying, ex vivo, a biological sample from the subject for the presence of a genetic marker or biomarker indicative of increased risk of developing a neurodegenerative disease or disorder.

In embodiments, the subject in need is one who is at risk of cognitive impairment due to chronic stress.

In embodiments, the subject in need is one who is at risk of cognitive impairment due to age. In embodiments, the subject is 50 years of age or older.

In accordance with any of the preceding embodiments, the agonist is preferably a positive allosteric modulator.

In accordance with any of the preceding embodiments, the agonist may be administered to the subject chronically for a period of days, weeks, months or years.

In accordance with any of the preceding embodiments, the pharmaceutical composition is an oral dosage form, such as a tablet or capsule, including sublingual dosage forms such as a sublingual tablet, strip, drop, spray, or lozenge. In some embodiments, the pharmaceutical composition is in the form of a dermal patch or nasal spray.

In accordance with any of the preceding embodiments, the agonist is 8-ethynyl-6-(2-fluorophenyl)-N,N,4-trimethyl-4H-benzo[f]imidazo[1,5-a][1,4]diazepine-3-carboxam, preferably (R)-8-ethynyl-6-(2-fluorophenyl)-N,N,4-trimethyl-4H-benzo[f]imidazo[1,5-a][1,4]diazepine-3-carboxamide, or a pharmaceutically acceptable salt thereof. In certain embodiments, the agonist may be selected from 8-ethynyl-6-(2-fluorophenyl)-N,N,4-trimethyl-4H-benzo[f]imidazo[1,5-a][1,4]diazepine-3-carboxamide, and pharmaceutically acceptable salts and enantiomeric mixtures thereof. In embodiments, the enantiomeric mixture consists of R and S isomers in a ratio of at least 80/20 R:S, more preferably 90/10, or 95/5, with the R isomer being in excess. In certain embodiments, the enantiomeric mixture consists of at least 50%, at least 80%, or at least 90% S enantiomer, for example in embodiments where a shorter-acting compound is desired.

In accordance with any of the preceding embodiments, the subject is preferably a human subject, but the subject may also be selected from a non-human mammal, for example, a dog, a cat, a horse, a cow, a mouse, a rat, etc. In some embodiments, the subject is a dog.

In embodiments, the subject is a human subject at risk for cognitive impairment or neurocognitive decline associated with age or chronic stress, or one who is at risk of developing a neurological disease or disorder.

The disclosure also provides the use of a pharmaceutical composition comprising an alpha5-GABAA receptor agonist in a method for preventing or delaying the onset of one or more symptoms of cognitive impairment or neurocognitive decline in an asymptomatic human subject at risk of developing cognitive impairment or neurocognitive decline, for example due to age or due to the subject's being at risk of developing a neurodegenerative disease or disorder, preferably wherein the agonist is a positive allosteric modulator, most preferably wherein the agonist is (R)-8-ethynyl-6-(2-fluorophenyl)-N,N,4-trimethyl-4H-benzo[f]imidazo[1,5-a][1,4]diazepine-3-carboxamide, or a pharmaceutically acceptable salt thereof.

DETAILED DESCRIPTION OF THE DISCLOSURE

Figure 1:
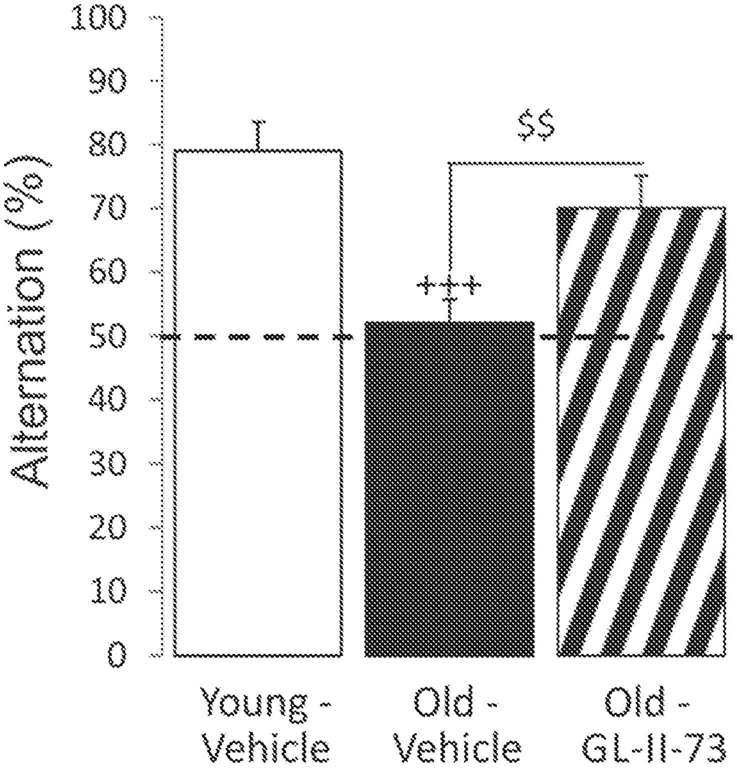
FIG. 1: Chronic administration of GL-II-73 reverses age-related working memory deficit in mice. Bars depict alternation as percentage in the Y maze test. Open bar, young mice administered vehicle only; black bar, old mice administered vehicle only; striped bar, old mice administered alpha5-GABAA receptor agonist, GL-II-73. Dollar sign ($$) indicates p=0.01.
Figure 2A:
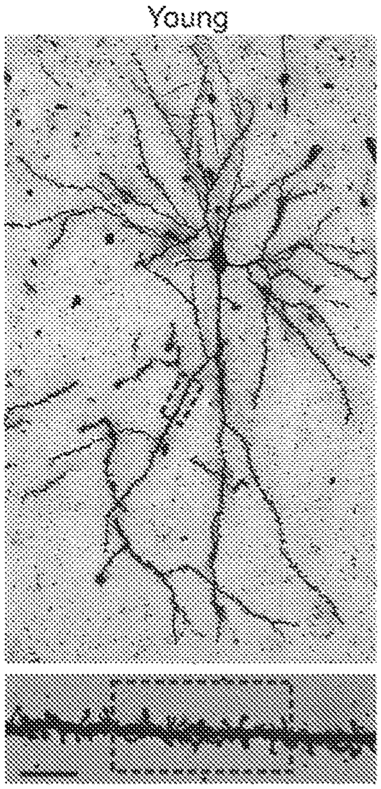
FIGS. 2A-D: Representative images of prefrontal cortex (PFC) pyramidal cells between groups (A) Young, (B) Old, and (C) Old plus treatment with alpha5-GABAA receptor agonist, GL-II-73 (Old+Treatment). Compared to young mice (A), aged mice showed reductions in spine counts of pyramidal cells (boxes within lower panels of A-C). Scale bar: 5 m. (D) Scheme of a dendrite with countable and uncountable spines for morphological analysis. Check marks represent countable spines; X's represent uncountable spines.
Figure 2B:
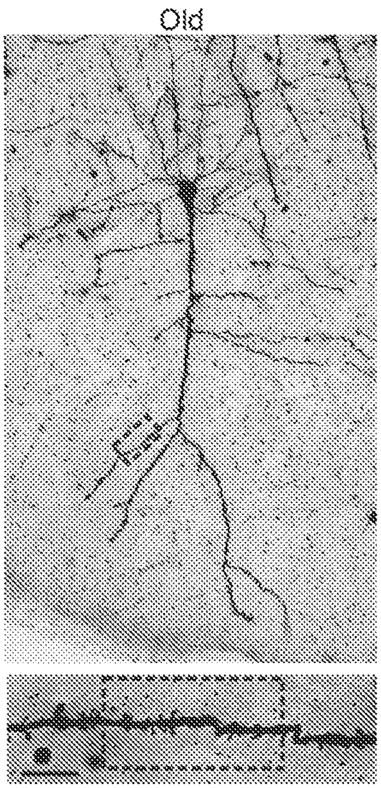
Figure 2C:
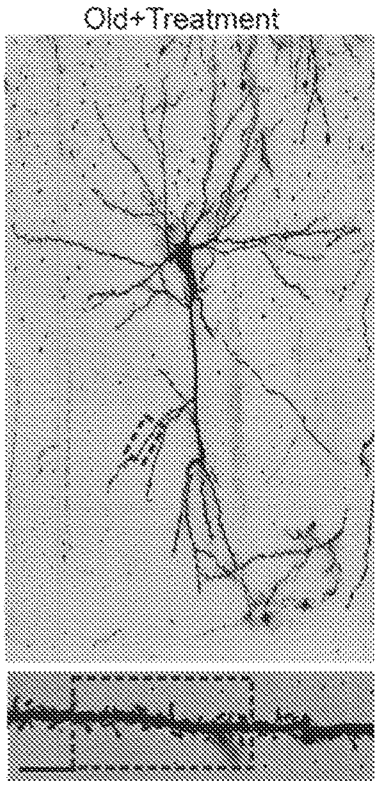
Figure 2D:
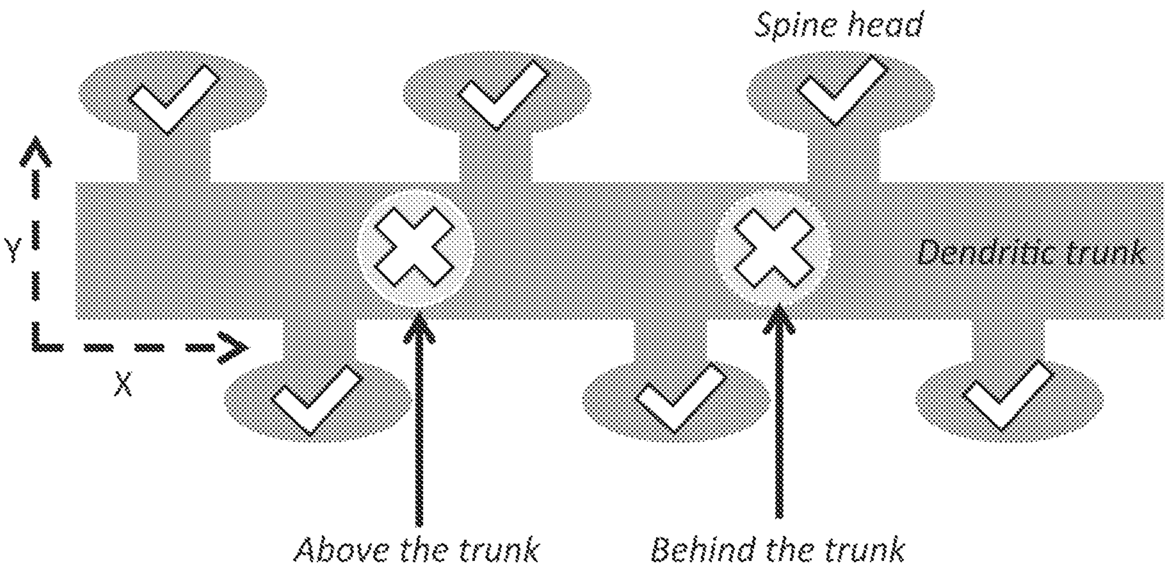

The present disclosure provides methods and related compositions for preventing, delaying, or reversing morphological changes in pyramidal neurons that occur incident to normal aging and underly cognitive impairment and neurocognitive decline, especially that associated with chronic stress, advanced age, and neurodegenerative diseases, such as Alzheimer's Disease ("AD"). The methods described here are based upon the chronic administration of alpha5-GABAA receptor agonists to slow or prevent deleterious morphological changes in pyramidal cells of the hippocampus and prefrontal cortex which changes eventually result in functional alterations that manifest as the cognitive impairment and neurocognitive deficits associated with conditions such as chronic stress, advanced age, and neurodegenerative diseases.

In the context of the present methods, an alpha5-GABAA receptor agonist is preferably administered to a subject in need prior to the onset of age or disease related morphological changes in pyramidal neurons and prior to symptoms of cognitive impairment or neurocognitive decline. For example, prior to the onset of symptoms such as memory loss, memory deficit, attention deficit, speech impairment, etc., especially in subjects at risk of cognitive impairment or neurocognitive decline, for example due to chronic stress or predisposition to a neurodegenerative disease or disorder, as discussed in more detail below.

As described here, an "agonist" of an alpha5-GABAA receptor is an agent that activates the receptor, resulting in the opening of the receptor's ion channel and allowing the selective passage of ionic chlorine through its pore. In this context, the term "agonist" may also include agents that increase the function of the receptor in the presence of its natural ligand, 7-aminobutyric acid (GABA). Such agonists may also be referred to as positive allosteric modulators.

alpha5-GABAA Receptor Agonists

In some embodiments of the methods described here, the alpha5-GABAA receptor agonist is a positive allosteric modulator. In some embodiments, the alpha5-GABAA receptor agonist is a small organic molecule.

In some embodiments, the small organic molecule agonist is a compound designated "GL-II-73", or a pharmaceutically acceptable salt thereof. The chemical name of GL-II-73 is 8-ethynyl-6-(2-fluorophenyl)-N,N,4-trimethyl-4H-benzo[f]imidazo[1,5-a][1,4]diazepine-3-carboxamide. The molecular formula of GL-II-73 is C23H19FN4O, and its molecular weight is 386.42 g/mol. GL-II-73 and methods for its synthesis are described in WO 2017/161370. The structure of the R enantiomer of GL-II-73 free base is shown below.

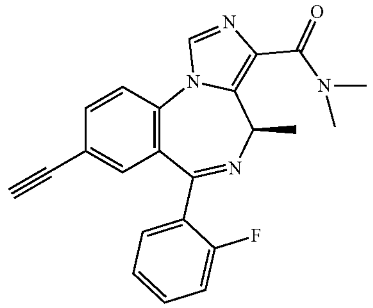 [SMILES: C#Cc1ccc2c(c1)C(c1ccccc1F)=N[C@H](C)c1c(C(=O)N(C)C)ncn1-2]

In some embodiments, the alpha5-GABAA receptor agonist for use in the methods described here is pharmaceutically acceptable salt, enantiomer, solvate, clathrate, hydrate, polymorph, prodrug, analog or derivative of GL-II-73.

The term "pharmaceutically acceptable salt" refers to a salt formed from, for example, a basic functional group of GL-II-73, such as an amine group, and a pharmaceutically acceptable inorganic or organic acid. Suitable pharmaceutically acceptable salts may include acid addition salts formed using acids such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, besylate, gentisinate, fumarate, gluconate, glucaronate, saccharate, formate, benzoate, glutamate, methanesulfonate, ethanesulfonate, benzenesulfonate, p-toluenesulfonate, and pamoate (e.g., 1,1'-methylene-bis-(2-hydroxy-3-naphthoate)) salts.

When a stereochemical depiction is shown, it is meant to refer to the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 95% or at least 99%. In some embodiments, the R enantiomer of GL-JJ-73 is preferred, for example due to its longer half-life compared to the S enantiomer, and the agonist compound is substantially free of the S enantiomer. In some embodiments, the S enantiomer is preferred, for example where a shorter-acting compound is desirable, and the agonist compound is substantially free of the R enantiomer. Compounds may be prepared by either stereospecific synthesis or by resolution using techniques known in the art, for example by formation of stereoisomeric pairs by salt formation with an optically active base, followed by fractional crystallization and regeneration of the free acid; or by formation of stereoisomeric esters or amides, followed by chromatographic separation and removal of the chiral auxiliary; or using a chiral HPLC column; or from kinetic resolution of the racemate of corresponding esters using lipase enzymes.

The term "polymorph" refers to solid crystalline forms of a compound or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

The term "hydrate" refers to a compound or a salt thereof, which further includes a stoichiometric or non-stoichiometric amount of water bound by non-covalent intermolecular forces.

The term "clathrate" refers to a compound or a salt thereof in the form of a crystal lattice that contains spaces (e.g., channels) that have a guest molecule (e.g., a solvent or water) trapped within.

The term "prodrug" refers to a derivative of a compound described herein that can hydrolyze, oxidize, or otherwise react under biological conditions (in vitro or in vivo) to provide a compound of the invention. Prodrugs may only become active upon such reaction under biological conditions, or they may have activity in their unreacted forms. Examples of prodrugs contemplated in this invention include, but are not limited to, analogs or derivatives of a compound described herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —$NO_2$, —ONO, or —$ONO_2$ moieties. Prodrugs can typically be prepared using well-known methods, such as those described by Burger's Medicinal Chemistry and Drug Discovery (1995) 172-178, 949-982 (Manfred E. Wolff ed., $5^{th}$ ed.).

The term "solvate" or "pharmaceutically acceptable solvate," refers to a solvate formed from the association of one or more solvent molecules to one of the compounds disclosed herein. The term solvate includes hydrates (e.g., hemi-hydrate, mono-hydrate, dihydrate, trihydrate, tetrahydrate, and the like).

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound. As used herein, the term "derivative" refers to compounds that have a common core structure, and are substituted with various groups as described herein.

In some embodiments, the alpha5-GABAA receptor agonist for use in the methods described here may be in the form of a pharmaceutical composition. A "pharmaceutical composition" is a formulation containing the compounds described herein in a pharmaceutically acceptable form suitable for administration to a subject, preferably a human subject. As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "unit dosage form" as used herein refers to physically discrete units suited as unitary dosages for the subject to be treated; each unit containing a predetermined quantity of active compound calculated to produce the desired therapeutic effect in association with the required pharmaceutical carrier. The specifications for the unit dosage forms of the invention are dictated by and directly dependent on the unique characteristics of the active compound and the particular therapeutic effect to be achieved. A unit dosage form can be an ampoule, a vial, a suppository, a dragee, a tablet, a capsule, an IV bag, a dermal patch, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). An effective amount of a pharmaceutical composition is that which provides an objectively identifiable improvement as noted by the clinician or other qualified observer. For example, alleviating a symptom of a disorder, disease or condition. As used herein, the term "dosage effective manner" refers to amount of a pharmaceutical composition to produce the desired biological effect in a subject or cell.

The pharmaceutical compositions can take any suitable form (e.g, liquids, aerosols, solutions, inhalants, mists, sprays; or solids, powders, ointments, pastes, creams, lotions, gels, patches and the like) for administration by any desired route (e.g, pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose); in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In some embodiments, the disclosure provides a pharmaceutical composition in the form of a nasal spray comprising an alpha5-GABAA receptor agonist, preferably a positive allosteric modulator of an alpha5-GABAA receptor, most preferably GL-II-73, or a pharmaceutically acceptable salt thereof.

In some embodiments, the disclosure provides a pharmaceutical composition in the form of a dermal patch comprising an alpha5-GABAA receptor agonist, preferably a positive allosteric modulator of an alpha5-GABAA receptor, most preferably GL-II-73, or a pharmaceutically acceptable salt thereof.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. In the case of tablets for oral use, carriers which are commonly used include lactose and corn starch. Lubricating agents, such as magnesium stearate, can also be added. For oral administration in a capsule form, useful diluents include lactose and dried corn starch. When aqueous suspensions and/or emulsions are administered orally, the compound of the present invention may be suspended or dissolved in an oily phase is combined with emulsifying and/or suspending agents. If desired, certain sweetening and/or flavoring and/or coloring agents may be added.

A pharmaceutical composition can be in the form of a tablet. The tablet can comprise a unit dosage of a compound of the present invention together with an inert diluent or carrier such as a sugar or sugar alcohol, for example lactose, sucrose, sorbitol or mannitol. The tablet can further comprise a non-sugar derived diluent such as sodium carbonate, calcium phosphate, calcium carbonate, or a cellulose or derivative thereof such as methyl cellulose, ethyl cellulose, hydroxypropyl methyl cellulose, and starches such as corn starch. The tablet can further comprise binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures.

The tablet can be a coated tablet. The coating can be a protective film coating (e.g. a wax or varnish) or a coating designed to control the release of the active agent, for example a delayed release (release of the active after a predetermined lag time following ingestion) or release at a particular location in the gastrointestinal tract. The latter can be achieved, for example, using enteric film coatings such as those sold under the brand name Eudragit®.

Tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine.

A pharmaceutical composition can be in the form of a hard or soft gelatin capsule. In accordance with this formulation, the compound of the present invention may be in a solid, semi-solid, or liquid form.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value.

Among the surfactants for use in the compositions of the invention are polyethylene glycol (PEG)-fatty acids and PEG-fatty acid mono and diesters, PEG glycerol esters, alcohol-oil transesterification products, polyglyceryl fatty acids, propylene glycol fatty acid esters, sterol and sterol derivatives, polyethylene glycol sorbitan fatty acid esters, polyethylene glycol alkyl ethers, sugar and its derivatives, polyethylene glycol alkyl phenols, polyoxyethylene-polyoxypropylene (POE-POP) block copolymers, sorbitan fatty acid esters, ionic surfactants, fat-soluble vitamins and their salts, water-soluble vitamins and their amphiphilic derivatives, amino acids and their salts, and organic acids and their esters and anhydrides.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a neurological disease, condition or disorder as described herein, one or more syringes, one or more applicators, or a sterile solution suitable for reconstituting a pharmaceutical composition of the present invention.

Methods of Preventing Neurocognitive Decline

As discussed above, the disclosure provides methods of preventing cognitive impairment and/or neurocognitive decline, for example as may be associated with chronic stress, aging, and neurological diseases and disorders such as Alzheimer's disease, amyotrophic lateral sclerosis, multiple sclerosis, Parkinson's disease, Huntington's disease, and frontotemporal degeneration.

In embodiments, the disclosure provides methods for preventing morphological changes in pyramidal neurons associated with cognitive impairment or neurocognitive decline in a subject, preferably a human subject, in need of such preventive intervention. The methods comprise administering to the subject an alpha5-GABAA receptor agonist, preferably a positive allosteric modulator of alpha5-GABAA receptors. The alpha5-GABAA receptor agonist is preferably administered to the subject chronically, meaning on an ongoing basis for a period of time. For example, in embodiments, the alpha5-GABAA receptor agonist is administered daily for a period of days, weeks, months or years to the subject. In some embodiments, the alpha5-GABAA receptor agonist is administered in the form of a nasal spray. In some embodiments, the alpha5-GABAA receptor agonist is administered in the form of a dermal patch. In some embodiments, the alpha5-GABAA receptor agonist is administered in the form of an oral dosage form, such as a tablet or pill, or a sublingual dosage form.

In embodiments, the subject in need of preventive intervention according to the methods described here is one who is at risk of developing a neurodegenerative disease or disorder selected from Alzheimer's disease, amyotrophic lateral sclerosis, multiple sclerosis, Parkinson's disease, Huntington's disease, and frontotemporal degeneration.

In the context of the present disclosure, the subject in need of preventive intervention according to the methods described here and who is identified as at risk of developing a neurodegenerative disease or disorder excludes subject who have already been diagnosed with a neurodegenerative disease or disorder. In some embodiments, the subject in need has not been diagnosed with acute depression. However, in some embodiments the subject in need may be one who has previously been diagnosed with depression but, at the time of being administered an alpha5-GABAA receptor agonist according to the methods described here, has not been diagnosed with depression and is not experiencing or suffering from a depressive episode. Depressive symptoms may be assessed, for example, using the Geriatric Depression Scale (GDS).

In embodiments, the subject in need of preventive intervention according to the methods described here is one who has been diagnosed with mild cognitive impairment ("MCI"). MCI is a condition manifesting as an increased impairment in cognitive skills relative to age-matched controls, but is distinct from the severe cognitive decline indicative of Alzheimer's disease. Patients with MCI have an increased risk of developing age-related cellular morphological changes and Alzheimer's disease. MCI can be diagnosed using neuropsychological tests. Petersen R. C. (2004). Mild cognitive impairment as a diagnostic entity. *J. Intern. Med.* 256, 183-194. The criteria include criteria self-reported corroborated memory deficits with preservation of the ability to perform everyday activities, a memory impairment based on a standard neuropsychological test, such as the Rey Auditory Verbal Learning Test (RAVLT), preserved global cognitive functions, and the exclusion of dementia. Global cognitive function may be assessed, for example, using the Addenbrooke's Cognitive Examination including orientation, attention, memory, verbal fluency, verbal, and visuospatial skills. The Trail Making test, Part A and Part B may be used to evaluate selective attention, executive functions, and cognitive flexibility. Dementia may be excluded, for example, using the Mini Mental State Examination (MMSE) with scores standardized for age and education.

In the embodiments, the subject in need of preventive intervention according to the methods described here is one who has been diagnosed with MCI and/or presents with an electroencephalogram (EEG) signature indicating an increased risk of developing Alzheimer's disease or related dementia, for example as described in Mazahari et al. "EEG oscillations during word processing predict MCI conversion to Alzheimer's disease". *NeuroImage: Clinical* (2018) 17:188-197.

In embodiments, the subject in need of preventive intervention according to the methods described here is one who is at risk of cognitive impairment due to chronic stress, for example, due to an event such as military deployment. In accordance with this embodiment, the methods encompass administering the alpha5-GABAA receptor agonist to the subject before the beginning of the event, as well as during the event, and after the event for a period of time, for example a period of days, weeks, months, or years. In embodiments, the subject in need due to an event such as military deployment or similar traumatic event is one who, at the time of being administered an alpha5-GABAA receptor agonist according to the methods described here, has not been diagnosed with post-traumatic stress syndrome.

In embodiments, the subject in need of preventive intervention according to the methods described here is one who is at risk of cognitive impairment due to age, for example one who is 50 years of age or older. In embodiments, the subject in need who is 50 years of age or older does not yet have evidence of the age related cellular morphological changes as described herein.

In embodiments, the subject in need of preventive intervention according to the methods described here is one who has not been diagnosed with, but who is at increased risk of developing, a neurodegenerative disease or disorder, the increased risk being relative to the risk of the general population. For example, a subject at increased risk may be one who has a genetic predisposition to a neurodegenerative disease or disorder. A genetic predisposition to a neurodegenerative disease or disorder can be determined, for example, by the presence of one or more genetic markers or biomarkers in a biological sample from the subject, for example a blood, plasma, cerebrospinal fluid, or tissue sample, and/or a family history of a neurodegenerative disease or disorder in the family of the subject. In embodiments, the biomarker may be in the form of a genetic variant predisposing to early onset familial Alzheimer's disease, for example a variant or isoform in one or more of the presenilin 1 (PS1) gene, the presenilin 2 (PS2) gene, the amyloid precursor protein (APP) gene, the apolipoprotein E (APOE) gene, for example APOE 4 which increases the risk of Alzheimer's disease. In embodiments, the biomarker may be one or more proteins associated with Alzheimer's disease, for example, amyloid-β peptide (Aβ), total tau (t-tau), and hyperphosphorylated tau (p-tau), detected, for example in cerebrospinal fluid from the subject. In embodiments, the subject at risk is one identified based on the subject's level of markers of cellular structure, for example by using positron emission tomography (PET) to measure the synaptic structure (SV2A ligand).

A genetic predisposition to a neurodegenerative disease or disorder can be also determined, for example, by analysis of a subject's family history or genealogy. In embodiments, the subject in need of preventive intervention according to the methods described here is one who is at increased risk of developing Alzheimer's disease due to the presence of Alzheimer's disease in one or more first or second degree relatives of the subject.

In embodiments, the subject in need of preventive intervention according to the methods described here is one who is at increased risk of developing Alzheimer's disease due to a diagnosis of MCI.

In embodiments, the subject in need of preventive intervention according to the methods described here is one who is at risk of developing a neurodegenerative disease or disorder, for example one who has one or more behavioral markers indicating an increased risk, relative to that of the general population. In embodiments, the subject at risk may be identified based on the subject's performance on one or more neuropsychological tests, for example as discussed above in connection with the diagnosis of MCI, and additionally include tests such as the Montreal Cognitive Assessment to assess cognitive performance.

The term "preventing" or "preventive" in the context of the methods described here is intended to encompass the prevention, or delay in onset of, age or disease related cellular morphological changes, and/or one or more symptoms associated with neurocognitive decline, such as memory loss, learning and memory deficit, attention deficit, speech impairment, deficits in executive control and planning, etc. Where one or more symptoms is delayed, the delay is measured relative to the time that the symptom would typically occur in an untreated age-matched individual, or in accordance with the natural history of a neurodegenerative disease and disorder.

A "subject" as used in the context of the methods described herein is preferably a human subject but may also include other mammals, for example a dog, a cat, a horse, a cow, a mouse, a rat, etc. In some embodiments, the subject is a dog.

All percentages and ratios used herein, unless otherwise indicated, are by weight. Other features and advantages of the present invention are apparent from the different examples. The provided examples illustrate different components and methodology useful in practicing the present invention. The present invention is further illustrated by the following examples.

EXAMPLES

We examined the impact of normal aging and the effects of chronic administration of an alpha5-GABAA receptor agonist, GL-II-73, in a mouse model of cognitive decline. Specifically, we examined in parallel both changes in cognitive function and changes in the morphology of pyramidal cells that are coincident with the onset of cognitive decline in this model system. Changes in cognitive function were assessed using the Y maze test as an index of working memory performance. Morphological changes in the pyramidal cells were evaluated by measuring dendritic shrinkage (length and segmentation) and dendritic spines (number and density). Two studies were conducted. The first examined the effects of chronic administration of GL-II-73 for 8 weeks. The second examined whether the morphological effects persisted after treatment was stopped, using a 1 week 'washout' period.

As discussed in more detail below, the results indicate that enhancing α5-GABAA-receptor activity by administration of GL-II-73 both alleviates cognitive deficits in the animals and reduces the morphological changes in pyramidal cells that otherwise occur during aging, and further that these morphological changes are long-lasting, particularly with respect to spine density.

Ongoing studies are extending these results to assess the delay of onset of neurodegenerative diseases such as Alzheimer's disease. These studies utilize the 5×FAD transgenic mouse model of Alzheimer's disease and are assessing the impact of amyloid beta accumulation and the effects of chronic administration of GL-II-73 on pyramidal cell morphology and the onset of cognitive decline. Preliminary results from the 5×FAD model indicate that the cognitive deficit is present at 6 months of age, and could be improved with an acute treatment of GL-II-73.

Detailed Results

Details of the animals, materials, and methods used are provided following the discussion section below. Briefly, all studies discussed below were conducted using three groups of animals designated "Young" (2 months of age at the beginning of the 8-week study, 4 months of age at time of testing; "Old" (22 months of age at beginning of study, 24 months of age at time of testing); and "Treatment" ("Old" mice who received GL-II-73 in the drinking water for 8 weeks prior to evaluation of cognitive ability and pyramidal cell morphology). The last study further included a fourth group of animals, "Treatment+Washout" which were treated the same as the "Treatment" group except that the GL-II-73 was removed for a 1 week "wash-out" period prior to evaluation of pyramidal cell morphology.

Chronic Administration of GL-II-73 Reverses Cognitive Decline Induced by Normal Aging The percentage of alternation during the Y maze test can be considered as an index of working memory performance (50% of alternation corresponding to a random alternation rate). FIG. 1 shows alternation in the Y maze test (%) for young mice (2 months of age at beginning of 8-week study, 4 months of age at time of testing) and old mice (22 months of age at beginning of study, 24 months of age at time of testing), with one group of old mice having received GL-II-73 in the drinking water for 8 weeks prior to the Y maze test, which group may be referred to herein as the "treatment" group. ANOVA analysis indicates a significant difference between all groups ($F(2;25)=11.34$; $p=0.0003$). Post hoc analysis revealed that aging significantly decreased the alternation rate ($p<0.001$) to 52.6% compared to young mice that have an alternation rate at 79.6%. Also, post hoc analysis revealed that old mice receiving GL-II-73 chronically in the drinking water for 8 weeks had higher alternation rate than old mice receiving only vehicle (water; $p=0.01$). This result suggests that chronic administration of the compound GL-II-73 improves alternation rate in old mice, suggesting that the treatment blocked or reversed working memory decline due to normal aging.

Chronic Administration of GL-II-73 Prevents Age-Related Morphological Changes in Dendritic Cells of the PFC Table 1 summarizes the results of a quantitative assessment of the morphological properties of Layer II/III pyramidal cells of prefrontal cortex (PFC) between Young, Old, and Treatment groups. FIG. 10 shows a schematic of a dendrite with countable and uncountable spines for morphological analysis. Check marks represent countable spines; X's represent uncountable spines. The total number of sampled neurons in the PFC study was 72 cells with a total of 1,888 dendritic segments, 193,698 total dendritic lengths (μm), and 199,529 spine counts, respectively. The overall spine density showed that Young mice contained the highest spine density, followed by mice in the Treatment group, with Old mice having the lowest spine density. The results show significant differences in total dendritic lengths, overall dendritic spine counts and overall dendritic spine density between the groups (ANOVA, $p<0.05$).

TABLE 1

Summary of morphological analysis of PFC between groups.

| Brain ID, treatment group | # Samples | Total segments | Total lengths (microns) | Total spine counts | Overall spinal density |
|---|---|---|---|---|---|
| Young, water | 4 | 629 | 68,973 | 79,195 | 1.15 |
| Old, water | 4 | 593 | 58,069 | 53,227 | 0.92 |
| Old, Treatment | 4 | 666 | 66,656 | 67,107 | 1.01 |
| Total | 12 | 1,888 | 193,698 | 199,529 | |

FIG. 2 shows representative images of a dendritic segment of pyramidal cells of the three groups, respectively. In the following qualitative observations, young mice exhibited more arborizations of the dendritic morphology than both the old and treatment groups (upper panel of FIGS. 2A-C). Moreover, young mice showed higher spine counts than both the old and treatment groups (lower panel of FIG. 2A-C). Note the treatment group also appeared to have more spine counts than old mice (see dashed line rectangles in panels below FIGS. 2A-C and quantitative comparisons of spine counts between groups as described below).

Figure 3A:
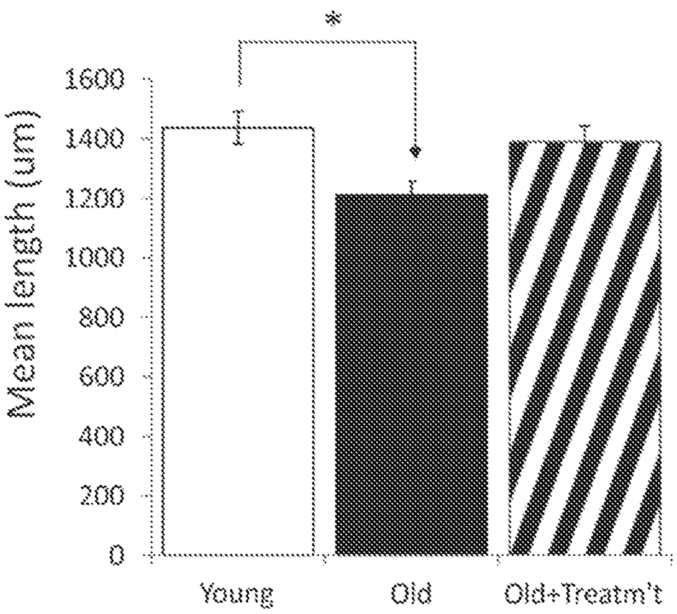
FIGS. 3A-B: Comparison of total dendritic lengths of pyramidal cells between groups. (A) total dendritic lengths between young, old and old plus treatment with alpha5-GABAA receptor agonist, GL-II-73 (Old+Treatment); (B) total dendritic lengths between young, old, and old+treatment groups of basal and apical dendrites. White bars (young); black bars (old); striped bars (old+treatment). Asterisk (*) indicates $p<0.05$ between comparators.

Reversal of age-related morphological changes in pyramidal cells by treatment with GL-II-73 was observed in apical dendrites, where α5-GABA-A receptors are located, and not in proximal dendrites, which are devoid of α5-GABA-A receptors. This was seen both in comparisons of total dendritic lengths (FIG. 3A-B) and total spine counts (FIG. 4A-B) of pyramidal cells between groups.

Figure 3B:
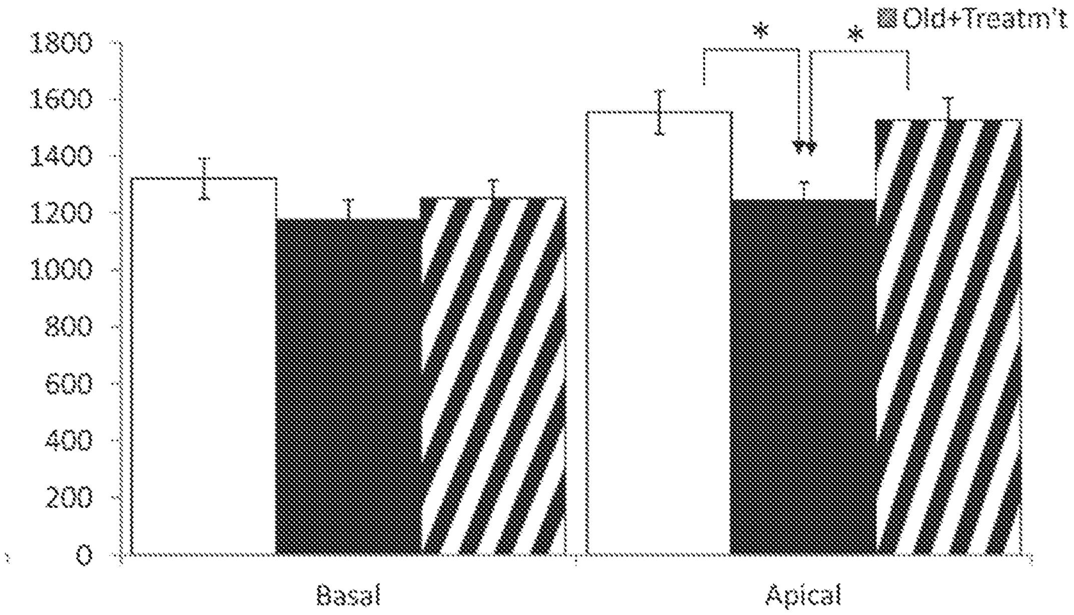

The total dendritic lengths (FIG. 3A) of old mice administered only vehicle showed a significant reduction compared to those of young mice (FIG. 3A, $p<0.05$), while there was no significant difference in total dendritic length between the young mice and the treatment group ($p>0.05$). In the break-down analysis, no difference was found in the basal dendrite between groups (FIG. 3B, left three bars $p>0.05$). In the apical dendrites, both young mice and the treatment group exhibited higher total dendritic lengths of apical dendrites than old mice, respectively (FIG. 3B, right three bars ($p<0.05$). There was no difference in this measure as between the young mice and the treatment group ($p>0.05$).

Figure 4A:
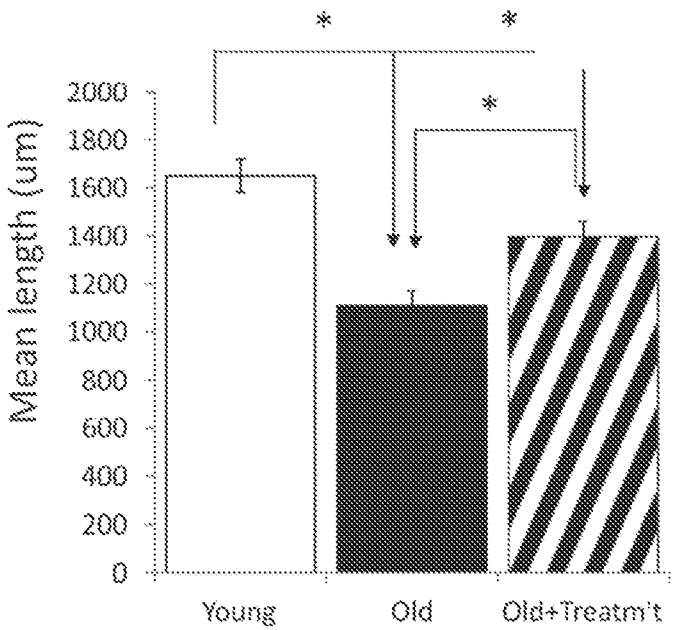
FIGS. 4A-B: Comparison of total spine counts of pyramidal cells between young, old, and old+treatment groups. (A) total dendritic lengths shown as mean length (μM); (B) total spine counts of apical (right three bars) and basal (left three bars) dendrites shown as mean count number. White bars (young); black bars (old); striped bars (old+treatment). Asterisk (*) indicates $p<0.05$ between comparators.
Figure 4B:
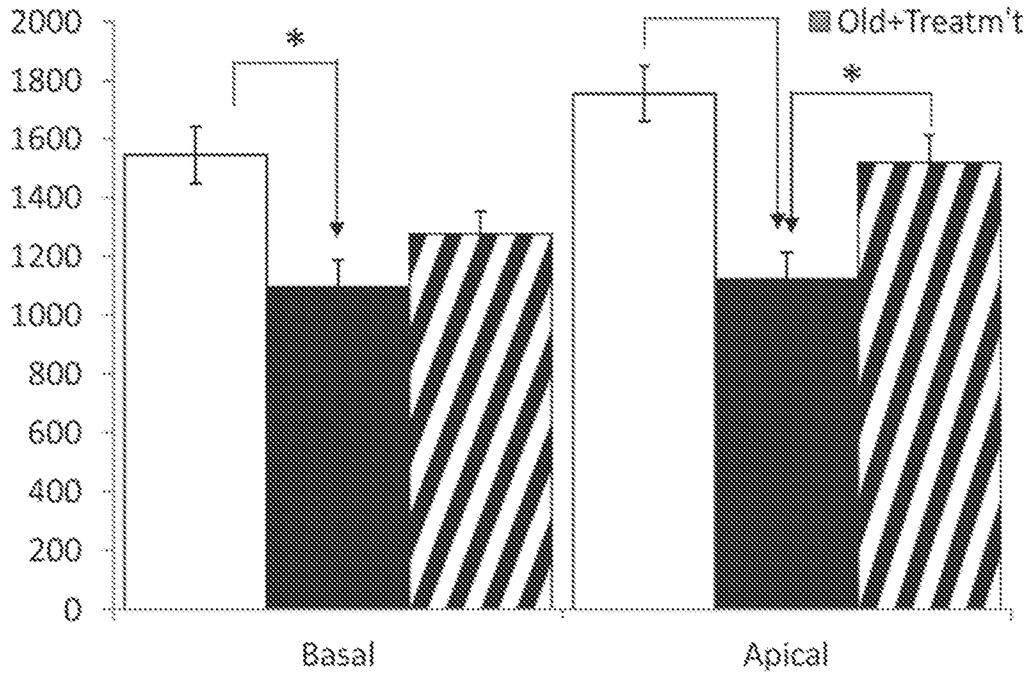

In the analysis of total spine counts, in comparison with young mice, there was a significant reduction in total spine counts of old mice and the treatment group, respectively (FIG. 4A, $p<0.05$). Also, the treatment group showed higher spine counts than old mice ($p<0.05$). In the breakdown analysis, only the old mice showed a significant decrease in the basal dendrite as compared to young mice (FIG. 4B, left three bars, $p<0.05$). In the apical dendrites, both young mice and the treatment group exhibited a higher spine count than old mice, respectively (FIG. 4B, right three bars, $p<0.05$). Note that there was no difference in both basal and apical dendrites between young mice and the treatment group ($p>0.05$).

Figure 5A:
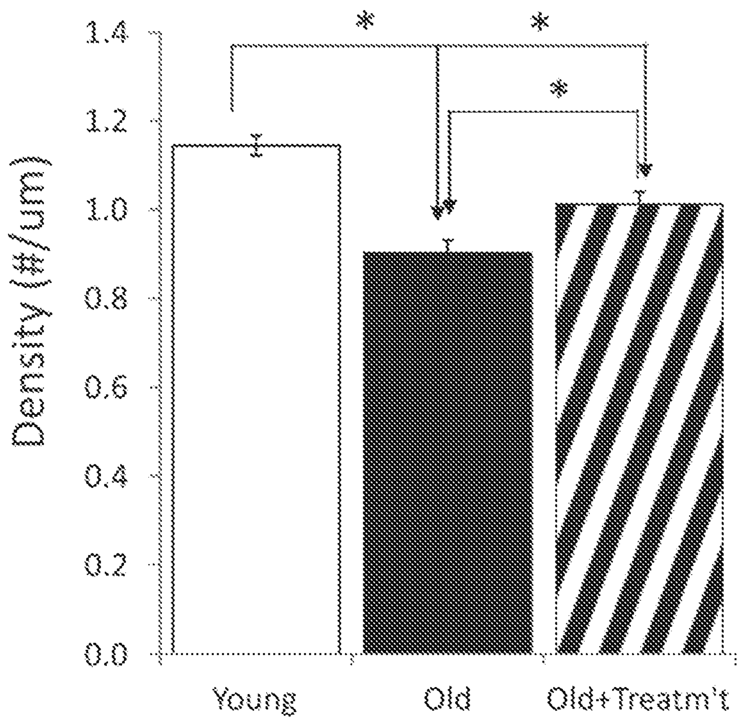
FIGS. 5A-B: Comparison of overall spine density of pyramidal cells between groups. White bars (young); black bars (old); striped bars old plus treatment with alpha5-GABAA receptor agonist, GL-II-73 (old+treatment).
Figure 5B:
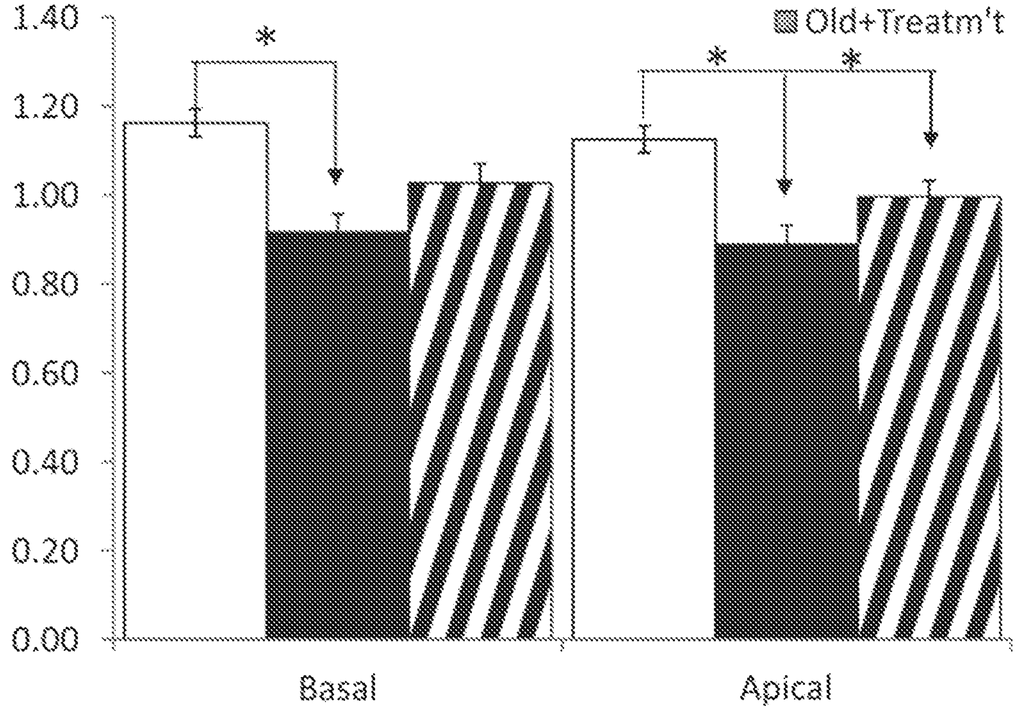

Similar to the results discussed above for total dendritic lengths and spine counts, in the analysis of overall spine density (FIG. 5A-B), a reversal of age-related morphological changes in pyramidal cells by treatment with GL-II-73 was observed in apical dendrites, and not in proximal dendrites, which are devoid of α5-GABA-A receptors. Thus, compared to young mice, there was a significant reduction in spine density of old mice and the treatment group, respectively (FIG. 5A, $p<0.05$). Also, the treatment group show a higher density than old mice ($p<0.05$)*. In the breakdown analysis, only old mice showed a significant decrease in the basal dendrite as compared to young mice (FIG. 5B, left three bars, $p<0.05$). In the apical dendrites, young mice exhibited a higher density than old mice and the treatment group, respectively (FIG. 5B, right three bars, $p<0.05$). There was no difference between old mice and the treatment group ($p>0.05$), which was likely due to the sample size being compromised by the breakdown analysis.

Figure 6A:
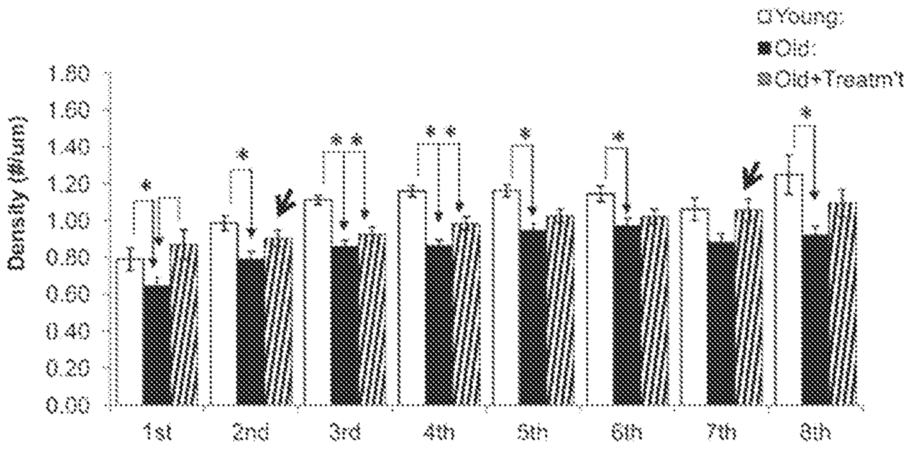
FIG. 6A-C: Comparison of spine density×branch orders of pyramidal cells between groups. (A) Overall spine density×branch order between groups; (B) Basel spine density×branch order between groups; and (C) apical spine density×branch order between groups. White bars (young); black bars (old); striped bars old plus treatment with alpha5-GABAA receptor agonist, GL-II-73 (old+treatment). Asterisk (*) indicates $p<0.05$ between comparators. Black arrows indicate groups that almost reached significance, $0.05<p<0.1$.
Figure 6B:
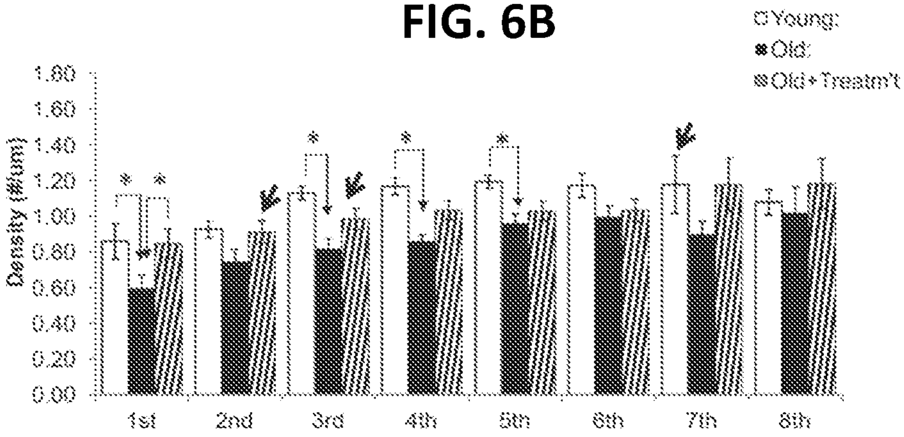
Figure 6C:
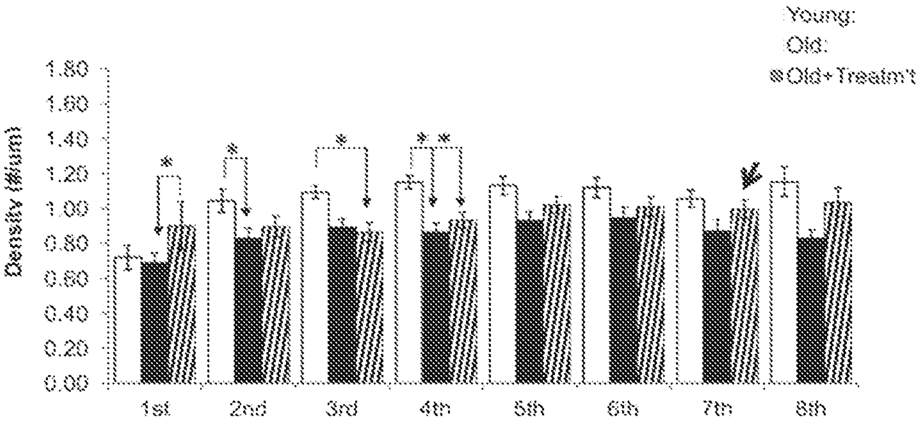

To further investigate the spine morphology of pyramidal cells, the spine density×branch orders was compared between groups. In FIG. 6, while ANOVA tests showed a significant difference in the spine density by branch orders between groups ($p<0.05$), post-hoc tests showed that young mice had a significantly higher spine density at the majority of branch orders than both age groups (FIG. 6A, $p<0.05$). Also, the treatment group showed a higher density at the $1^{st}$ branch order than old mice ($p<0.05$). In the breakdown analysis, young mice showed a higher density at the $1^{st}$, $3^{rd}$ to $5^{th}$ branch order of basal dendrites than old mice (FIG. 6B, $p<0.05$). Note that the treatment group showed a significantly higher density at the $1^{st}$ branch order than old mice ($p<0.05$). In the apical dendrites (FIG. 6C), young mice showed a higher density at the $2^{nd}$ and $4^{th}$ orders than old mice, and at the $3^{rd}$ and $4^{th}$ orders than the treatment group, respectively ($p<0.05$). Note that the treatment group showed a higher density at the $1^{st}$ order than old mice ($p<0.05$), and this trend of increase was also observed at varying branch orders of dendritic fields (arrows, $p>0.05$).

Figure 7A:
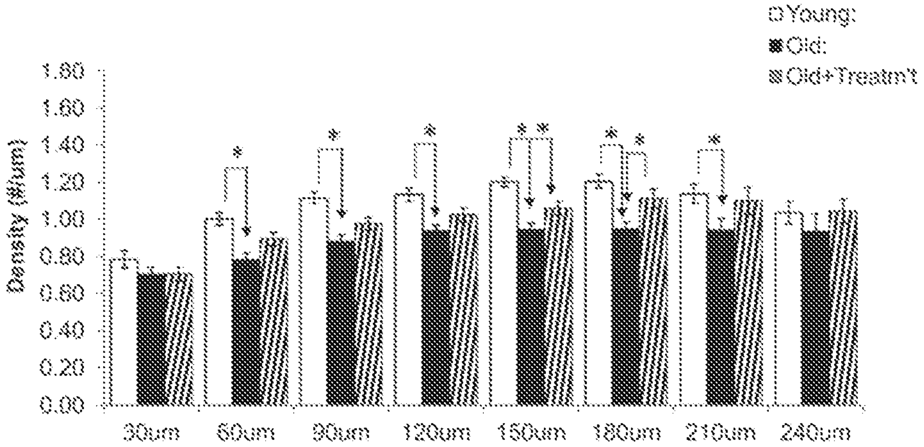
FIG. 7A-C: Comparison of spine density×every 30 m interval from the soma of pyramidal cells between groups. (A) overall spine density every 30 m between groups; (B) basal spine density every 30 m between groups; and (C) apical spine density every 30 m between groups. White bars (young); black bars (old) striped bars old plus treatment with alpha5-GABAA receptor agonist, GL-II-73 (old+treatment). Asterisk (*) indicates $p<0.05$ between comparators.
Figure 7B:
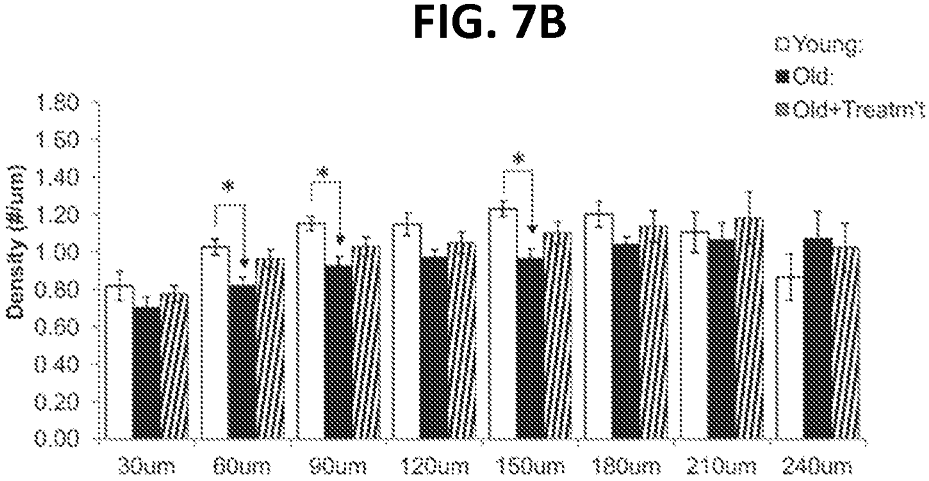
Figure 7C:
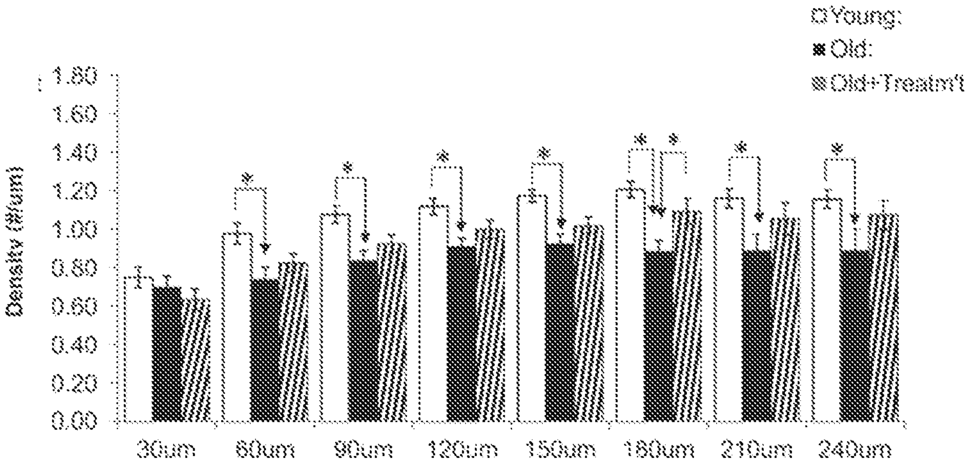

Sholl analysis: In the analysis of Frequency of intersections×every 30 micron interval from the cell body, or "soma", while ANOVA tests showed a significant difference in the spine density between groups ($p<0.05$), post-hoc tests showed that young mice had a significantly higher density at the majority (60-240 um interval from soma) of the dendritic fields than old mice and at 150 micron interval from soma than the treatment group, respectively (FIG. 7A, $p<0.05$). The treatment group showed a higher density at 180 micron interval from soma than old mice ($p<0.05$). In the breakdown analysis, young mice showed a higher density at 60-90 micron and 150 micron interval from soma of basal dendrites than old mice (FIG. 7B, $p<0.05$). In the apical dendrites (FIG. 7C), young mice showed a higher density at 60-240 micron from soma of the dendritic fields than old mice ($p<0.05$). Note that the treatment group showed a higher density at 180 micron interval from soma of the dendritic field than old mice ($p<0.05$).

Figure 8A:
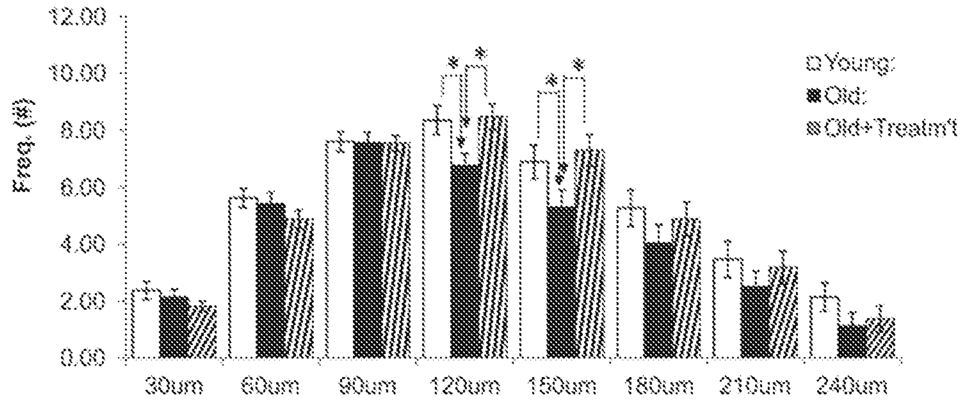
FIG. 8A-C: Comparison of Frequency of Intersections×every 30 m interval from the soma of pyramidal cells between groups. (A) overall frequency of interactions every 30 m between groups; (B) basal frequency of interactions every 30 m between groups; and (C) apical frequency of interactions every 30 m between groups. White bars (young); black bars (old) striped bars old plus treatment with alpha5-GABAA receptor agonist, GL-II-73 (old+treatment). Asterisk (*) indicates $p<0.05$ between comparators. Black arrows indicate groups that almost reached significance, $0.05<p<0.1$.
Figure 8B:
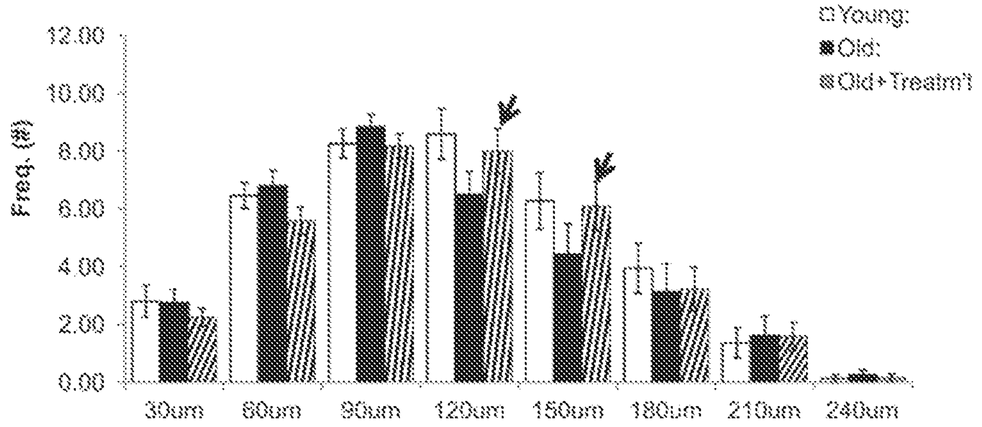
Figure 8C:
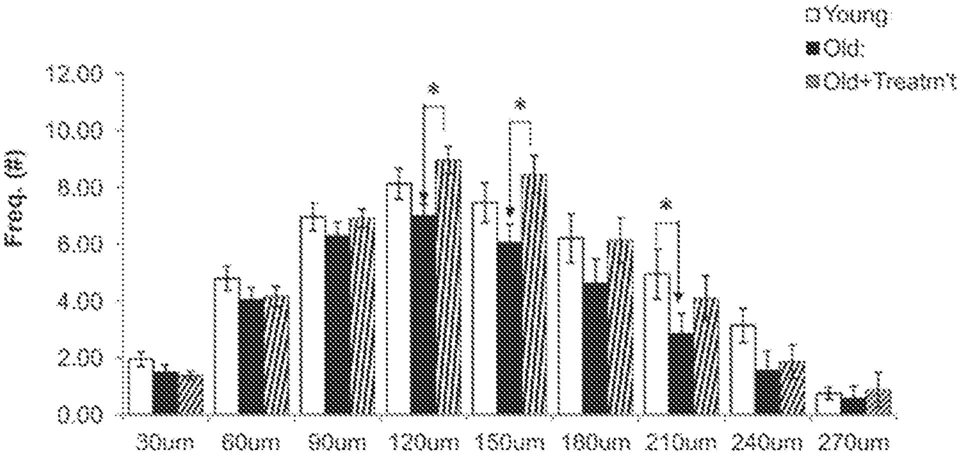

In the analysis of the frequency of interactions×30 micron interval relative to soma (FIG. 8), while ANOVA tests showed a significant difference in the frequency between groups ($p<0.05$), post-hoc tests showed significant reductions at a distance of 120-150 micron from the soma between old and young mice as well as between old and the treatment group, respectively (FIG. 8A, $p<0.05$). In the breakdown analysis, there no evidence of difference between groups, though a trend of decrease was found at 120-150 micron interval from soma between Old and Young as well as old and the treatment group, respectively (arrows in FIG. 8B, $p>0.05$). In the apical dendrites, (FIG. 8C), while young mice showed a higher frequency of intersections only at 210 micron interval from soma than old mice ($p<0.05$), the treatment group showed a higher frequency at 120-150 micron interval from soma than old mice ($p<0.05$), whereas there was no difference between young and any age groups ($p>0.05$). In conclusion, the above findings presented evidence of changes in morphological properties of layer II/III pyramidal cells of PFC between groups.

Chronic Administration of GL-II-73 Prevents Age-Related Morphological Changes in Dendritic Cells of the CA1 Region of the Hippocampus As shown in the data presented in FIGS. 3-8 and discussed above, morphological comparisons of Layer II/III pyramidal cells of the prefrontal cortex (PFC) between old, young, and treatment groups demonstrated significant differences with treatment in the apical dendrites, which are the cells that contain α5-GABA-A receptors, the target of GL-II-73.

Figure 11A:
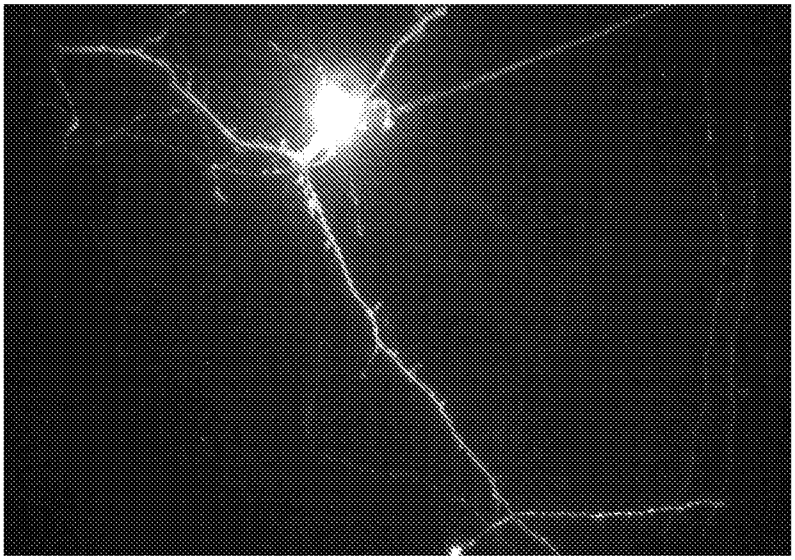
FIG. 11A-B: Photo of GFP-expressing neuron cultured in the absence (A) or presence (B) of GL-II-73 (1 uM) showing longer dendrites and more spines in the presence of GL-II-73.
Figure 11B:
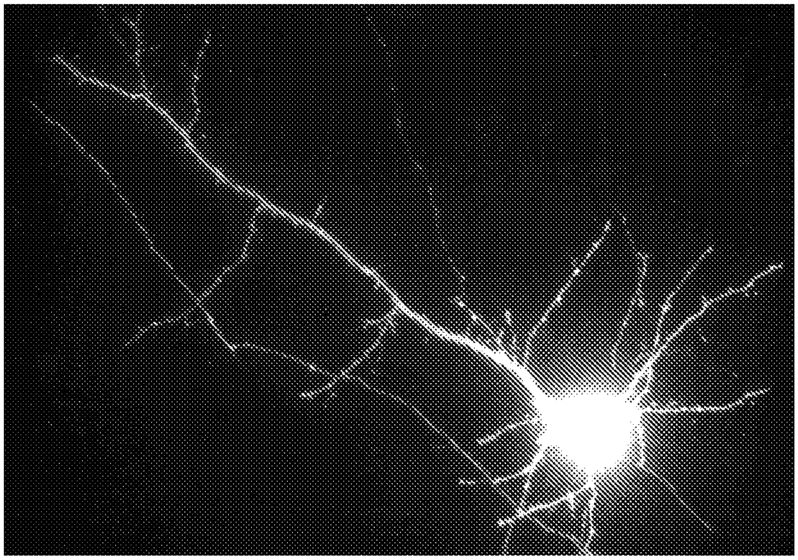
Figure 12:
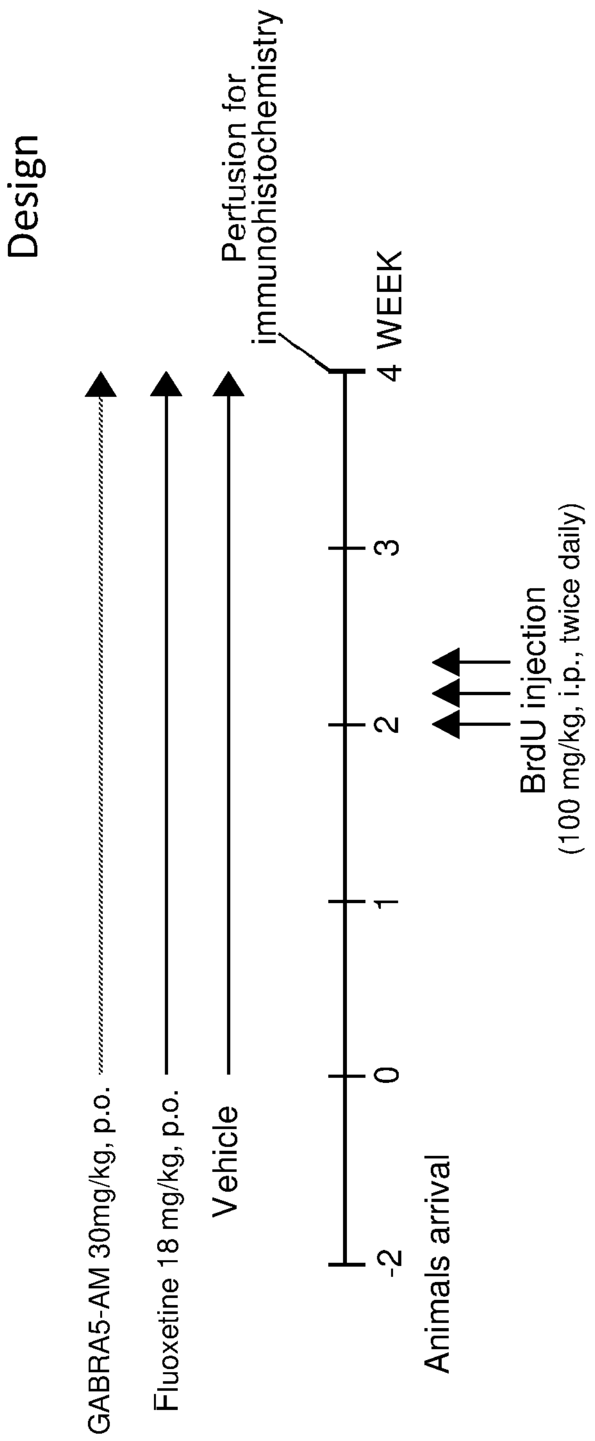
FIG. 12: Schematic of experimental design for analysis of neurogenesis in the SV129 mouse model.

We confirmed and extended these findings by conducting similar analyses of pyramidal cells in a different brain region, namely the CA1 region of the hippocampus, using the same animals. In brief, both groups of aged mice exhibited significant changes in spine morphology of CA1 of the hippocampus pyramidal cells as compared to young mice, including total dendritic lengths, total spine counts and overall spine density. The treatment group showed a relatively higher spine density than the untreated group of old mice. As observed above for the pyramidal cells of the PFC, the morphology of the CA1 pyramidal cells in the treatment group was very similar to that of the young mice. In addition, in comparisons of (i) Spine density×Branch orders and (ii) Spine density×30 um interval from soma between groups, Young mice showed (i) a higher spine density at the majority of branch orders and (ii) a higher density at the majority of dendritic fields compared to both aged groups. In comparison of Frequency of Intersections×30 um interval from soma between groups, both Young and Old+Treatment mice showed a higher frequency of intersections at the middle (120 um to 180 um) of the dendritic field than Old mice. Note that Old+Treatment mice exhibited a higher frequency at 120 um-150 um, basally and at 150 um-180 um, apically. The positive correlation between the morphological changes observed in each of the three groups of animals in both regions of the brain, CA1 vs PFC brain regions is shown in FIGS. 11-12. This positive correlation of morphological changes across these two regions of the brain indicates a common factor underlying the effects in both regions.

Figure 9A:
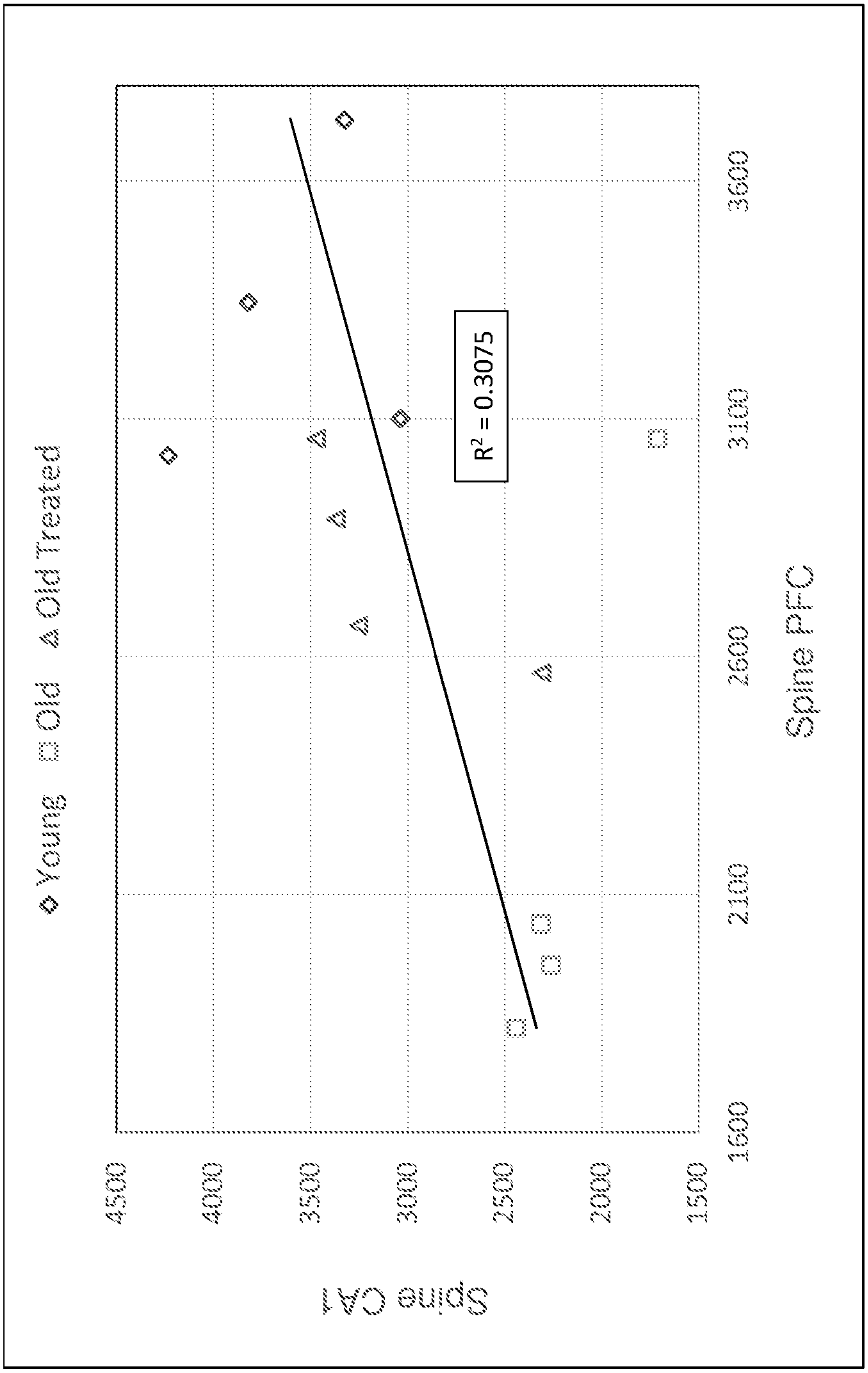
FIG. 9A-C: Correlation of spine counts (A, total; B, apical; C, basal) between pyramidal cells of prefrontal cortex (PFC) and CA1 pyramidal cells of the hippocampus. Positive correlations were seen in all three sets of data (young, diamonds; old, squares; treatment, triangles) but the correlation reached statistical significance only for the apical cells (panel B). (A) Total spine counts: $r^2=0.3075$, $r=0.554488$, $p=0.06$; (B) Apical spine counts: $r^2=0.3571$, $r=0.597539$, $p=0.04$, and (C) Basal spine counts: $r^2=0.2138$, $r=0.46235$, $p=0.13$.
Figure 9B:
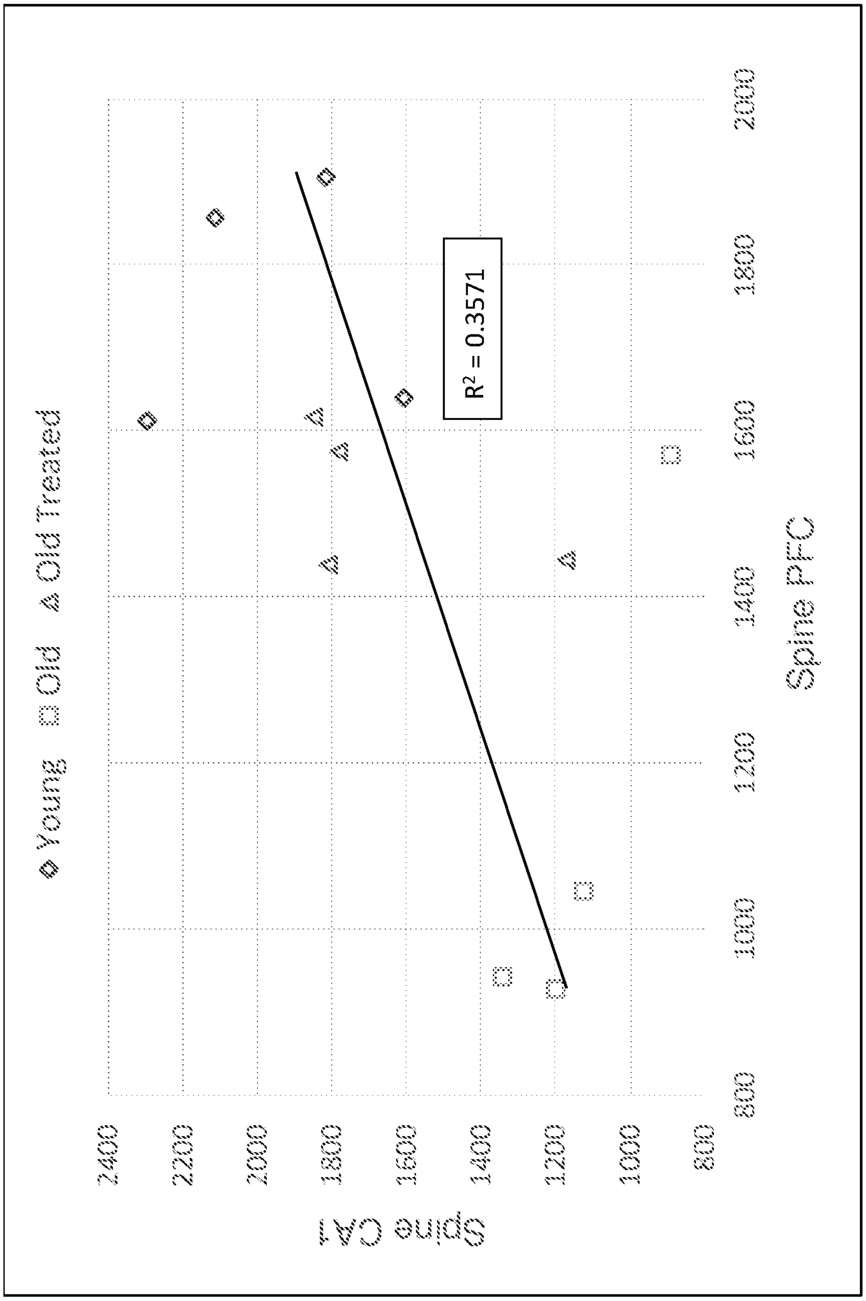
Figure 9C:
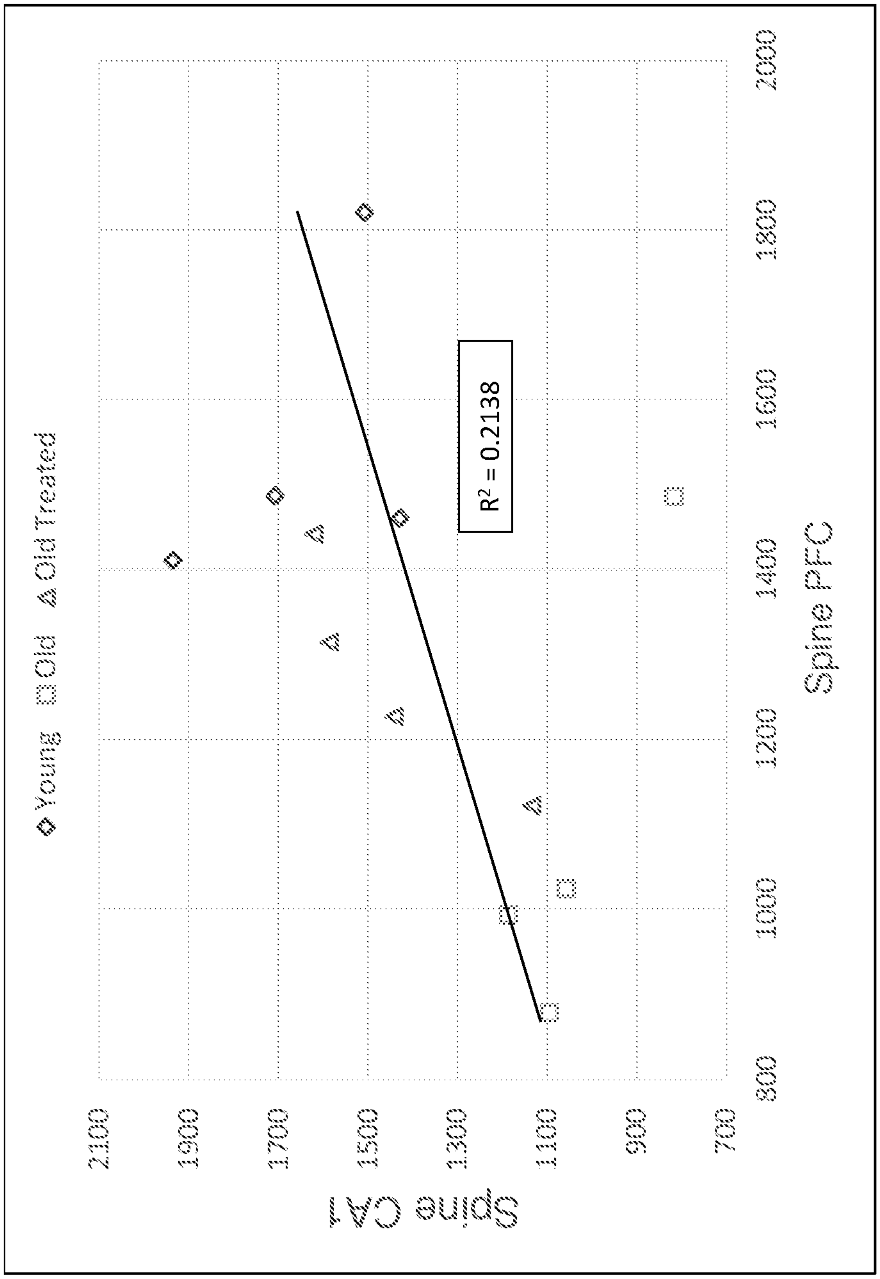
Figure 10A:
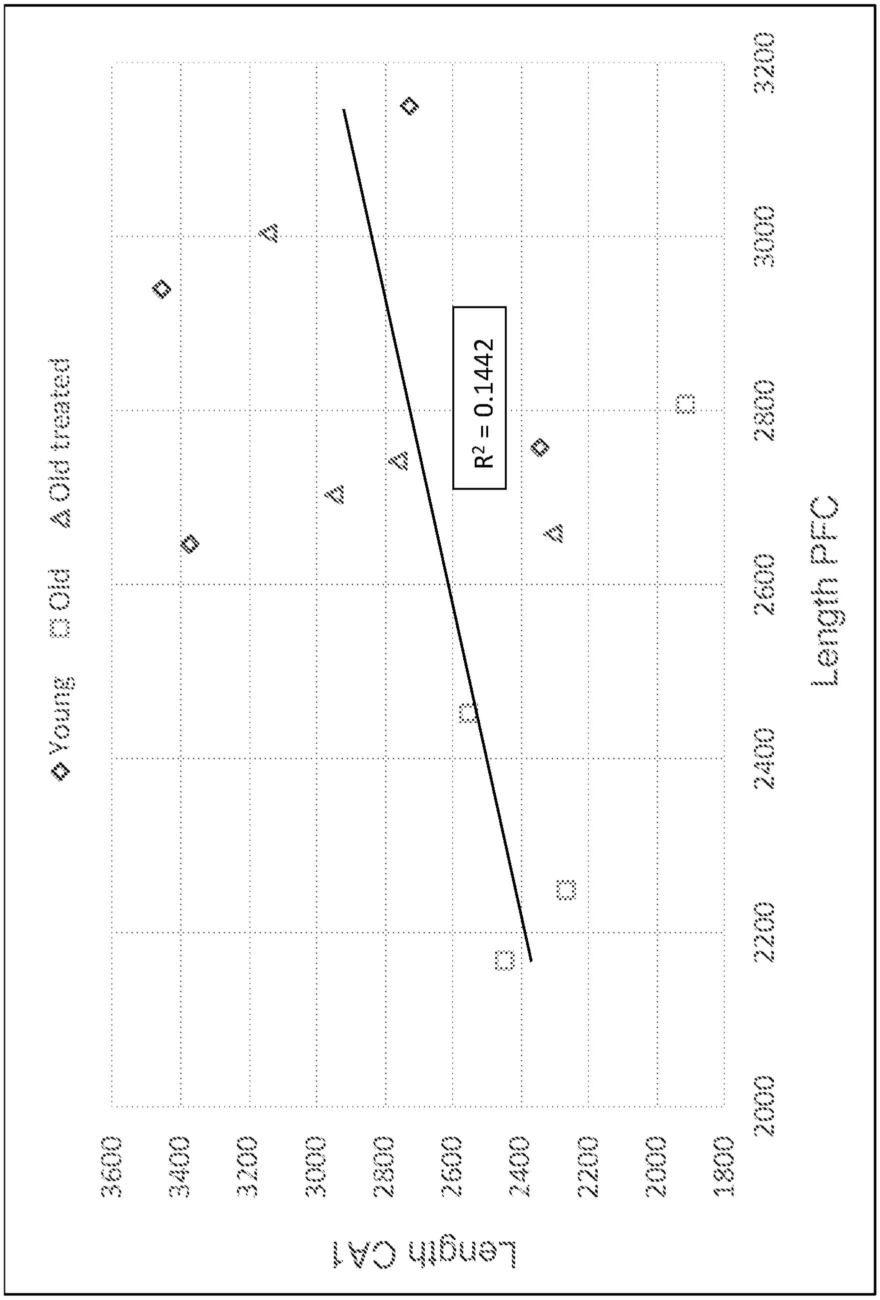
FIG. 10A-C: Correlation of dendritic length (A, total; B, apical; C, basal) between pyramidal cells of prefrontal cortex (PFC) and CA1 pyramidal cells of the hippocampus. Positive correlations were seen in all three sets of data but the correlation reached statistical significance only for the apical cells (panel B). (A) Total dendritic length: $r^2=0.1442$, $r=379686$, $p=0.22$; (B) Apical dendritic length: $r^2=0.3324$, $r=0.576536$, $p=0.04$, and (C) Basal dendritic length: $r^2=0.0005$, $r=0.02177$, $p=0.94$.
Figure 10B:
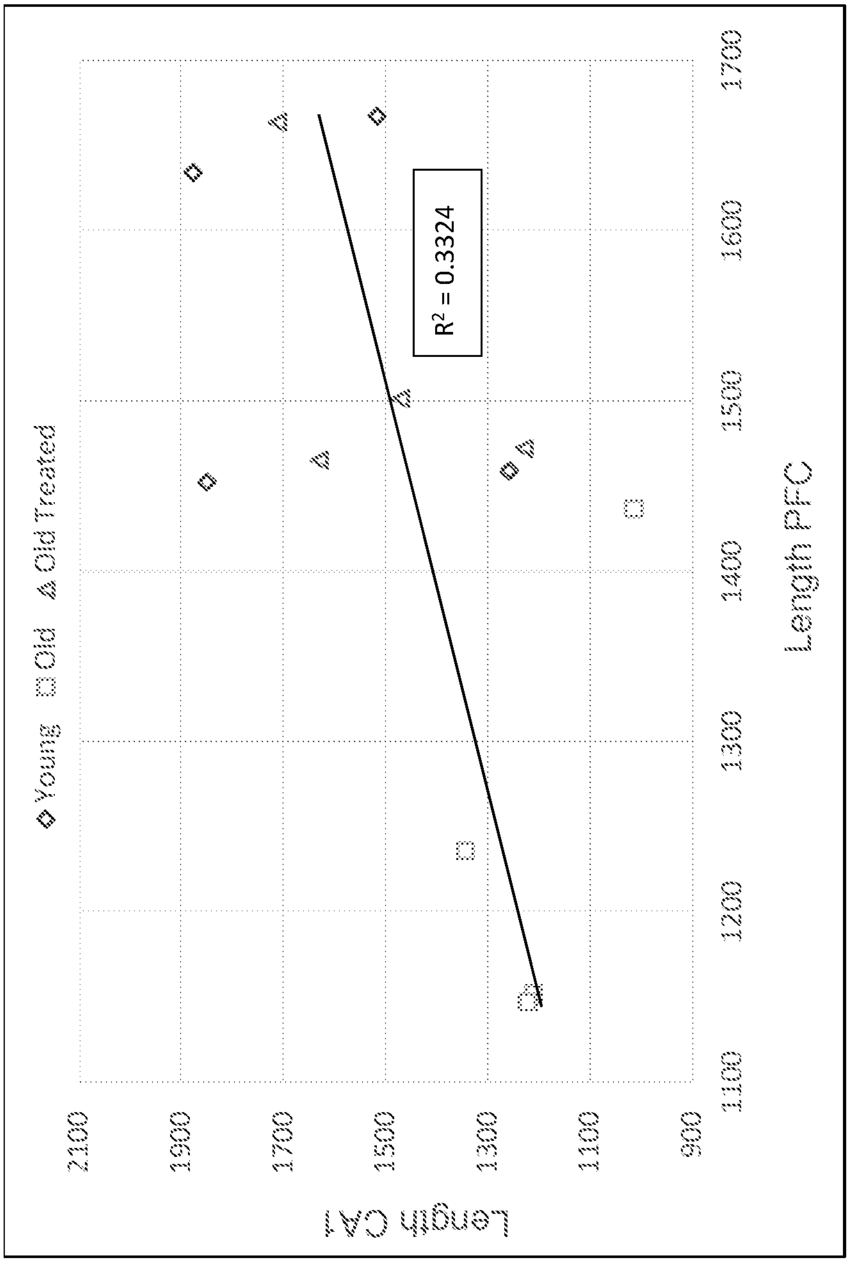
Figure 10C:
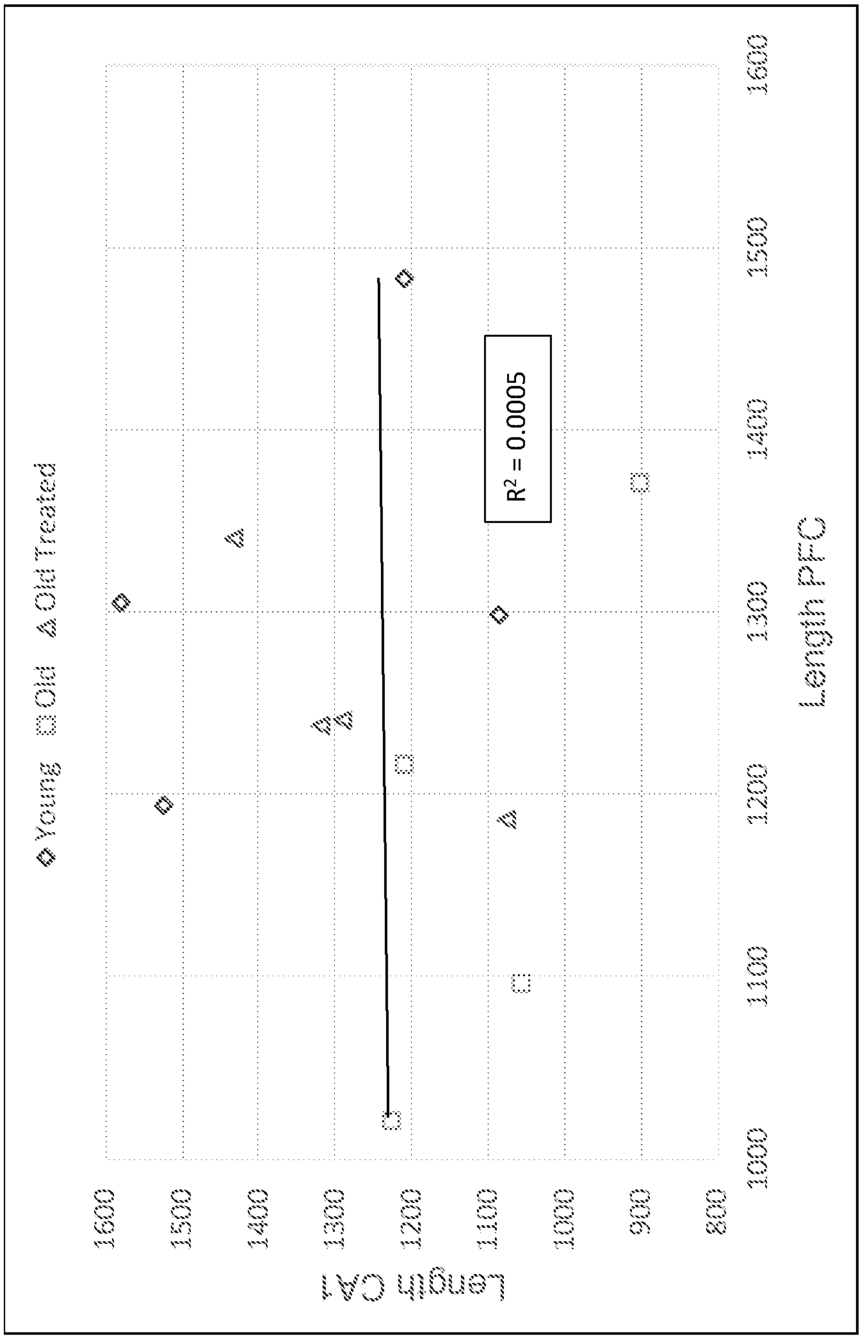

There was a significant correlation between the apical spine counts and apical dendritic lengths of PFC pyramidal cells and CA1 pyramidal cells in treatment groups, indicating that treatment affects the hippocampal-prefrontal cortex circuit (HIP-PFC) for the reversibility of aging. In brief, the average spine count and average dendritic length were calculated from 6 cells per animal in each group (young, old, old+treatment). As shown in FIG. 9A-C, the correlation between the total spine count in the PFC and CA1 is almost significant ($p=0.06$). But the correlation reaches statistical significance when we consider only the spine count from the apical segment of the dendritic cells ($p=0.04$) where the α5-GABA-A receptors are located. These data indicate that spine density in the CA1 and in the PFC are dynamically linked, meaning that if a condition or treatment increases the spine density in one region, it is likely to increase it in the other region as well. Similarly, and as shown in FIG. 10A-C, although the correlation between total dendritic length in the PFC and CA1 is not significant ($p=0.22$), the correlation between the lengths of the apical segments of the dendritic cells, where the α5-GABA-A receptor is located, is significant ($p=0.04$).

Acute Treatment with GL-II-73 Affects Morphology of Cultured Pyramidal Neurons

We next conducted in vitro experiments to determine whether acute treatment with GL-II-73 was able to affect the morphology of cultured pyramidal neurons, specifically whether treatment increased dendritic length and spine density in vitro. Transgenic mice were generated to express a fluorescent protein (GFP) only in pyramidal neurons. Embryos were collected at E17, and brain homogenates were plated and cultured under suitable conditions for neuronal growth. Following 2 weeks of incubation and growth, the compound GL-II-73 (1 μM) or vehicle was applied and left for 24 hrs. Isolated cells were then used to image the entire neuron and visualize dendrites and spines on a single neuron. As shown in FIG. 11A-B, the initial data indicates that treatment with GL-II-73 increases both dendritic length and spine density, even in cultured neurons. Comparing panel A (vehicle, 0.01% DMSO) with panel B (GL-II-73 (1 μM) of the figure, it can be seen that the neuron cultured with GL-II-73 has longer dendrites and more spines (little dots on the dendrites).

GL-H-73 Promotes Neurogenesis in Mouse Model

We next assessed the effects of GL-II-73 on neurogenesis using the SV129 mouse model Kim et al. 2017. *Neural Plasticity*, doi.org.10.1155/2017/5863258. Specifically, we assessed the effects of treatment on neuronal cell proliferation, survival, and maturation. It is now recognized that neurogenesis occurs not only during development, but also in the adult brain. In particular, neurogenesis has been found to occur both in the hippocampi and amygdala of adult humans. Specifically, adult neurogenesis is known to occur in three regions in the mammalian brain: (i) the subgranular zone (SGZ) of the dentate gyrus in the hippocampus, which is a region that is involved in regulating learning and memory; (ii) the subventricular zone (SVZ), which is situated throughout the lateral walls of the brain's lateral ventricles; and (ii) the amygdala. New neurons born in the SGZ migrate into the granule cell layer of the dentate gyrus and eventually become granule cells. These newborn neurons integrate into the existing circuitry and receive functional input. Adult neurogenesis in the hippocampus is therefore defined as the progression from neural stem cell to mature dentate granule neuron. All stages of adult neurogenesis are regulated by physiological activity, including the proliferation, differentiation, fate determination of adult neural stem cells (NSCs) and progenitors, and the survival, maturation, and integration of newborn neurons.

The stages of neurogenesis can be broken down into (i) proliferation, (ii) survival of the newly formed cells, and (iii) their maturation. Each can be evaluated using specific markers for proliferation, survival, and maturation. KI67 can be used as a marker of proliferation, as it shows when the cells are maintaining chromosomes separated, i.e. splitting into 2 cells (proliferating). BrdU can be used to show survival of the newly proliferating cells since it is incorporated into the newly synthesized DNA of replicating cells and is then maintained in the newly formed cells. Thus, quantitative immunohistochemistry against BrdU is used as a proxy of survival. Finally, doublecortin can be used as a proxy of maturation. Previous studies have shown that all steps of neurogenesis were down regulated in the SV129 mice, and further that chronic treatment with fluoxetine, a first line monoaminergic antidepressant, increased the neurogenesis in this mouse model. We therefore used this model system to assess the effects of chronic treatment with GL-II-73 on neurogenesis. The experimental design is shown in FIG. 12.

Figure 13A:
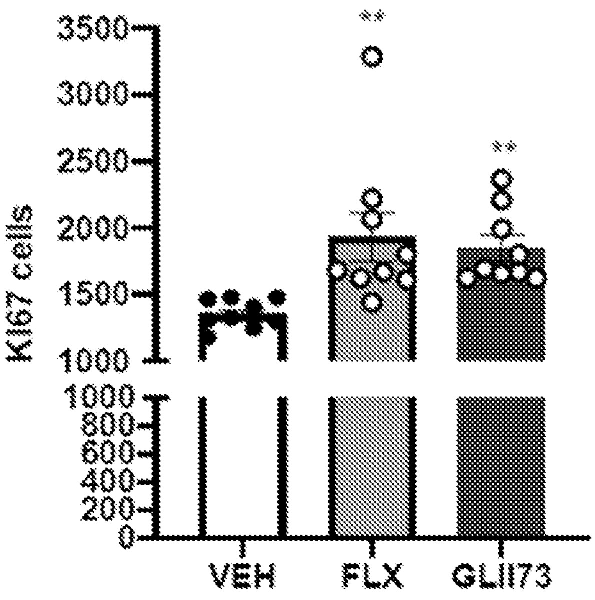
FIG. 13A-B: Proliferation (A) and survival (B) of neurons in the SV129 model for vehicle (VEH, white bars), fluoxetine treated (FLX, gray bars) and GL-II-73 treated (GLII73, dark gray bars) groups. Compared to VEH, both FLX and GL-II-73 increased the number of K167-positive cells ($F_{(2;23)}=5.08$; $p<0.05$) suggesting an increase in proliferation with both treatments (FLX: $p<0.001$; GL-II-73: $p<0.05$). Compared to VEH, only FLX increased BrdU-positive cells.
Figure 13B:
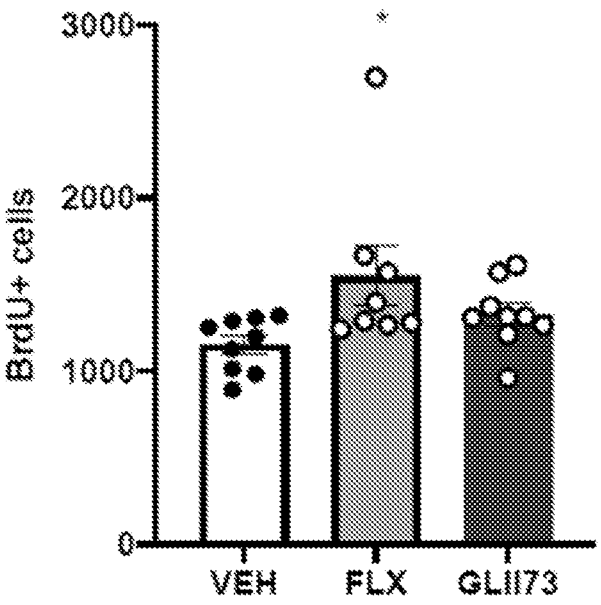
Figure 14A:
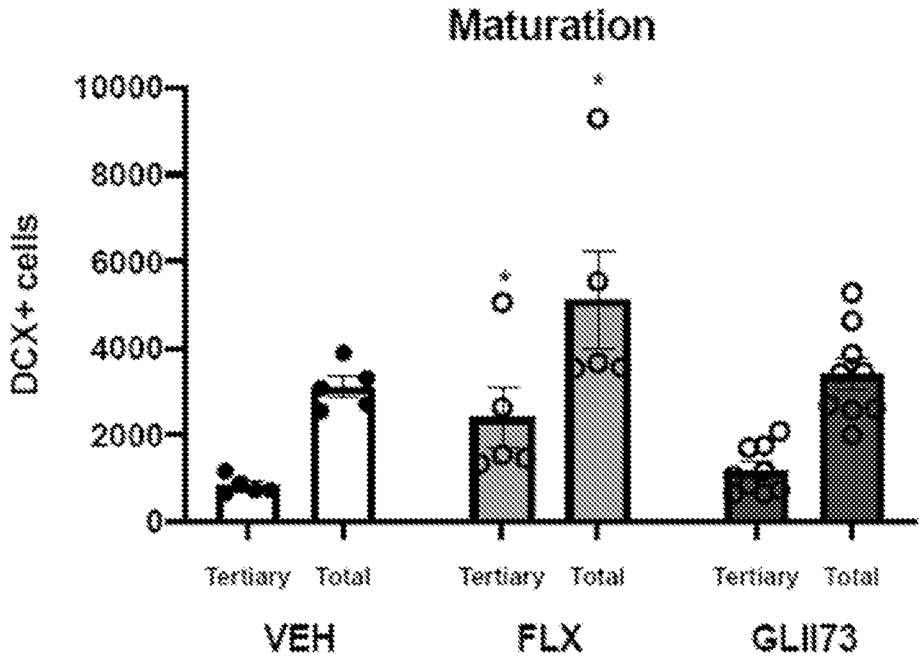
FIG. 14A-B: Neuronal cell maturation, measured as positive doublecortin (DCX) labeling in the SV129 model for vehicle (VEH, white bars), fluoxetine-treated (FLX, gray bars) and GL-II-73-treated (GLII73, dark gray bars) groups. DCX+cells were subcategorized according to their dendritic morphology: DCX+cells with primary or secondary, but no tertiary dendritic processes, and, DCX+cells with complex, tertiary dendrites. The maturation index was defined as the ratio of DCX+cells possessing tertiary dendrites over the total DCX+cells. (A) The number of DCX+cells was increased with FLX compared to VEH ($ps<0.05$). (B) The maturation index shows an increase with both FLX and GL-II-73 ($ps<0.01$), suggesting an increase in maturation and complexity of neurons when exposed to FLX or GL-II-73.
Figure 14B:
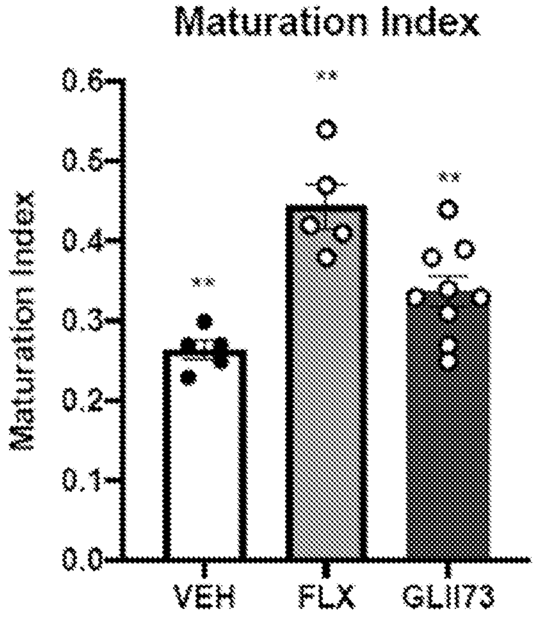

As shown in FIG. 13A, chronic GL-II-73 treatment (4 weeks) increased the proliferation of new cells, as shown by the increased in KI67 labeling in SV129 mice. Chronic GL-II-73 treatment also increased survival as shown by the increased in BrdU labeling in SV129 mice, as shown in FIG. 13B, even though not reaching significance. As shown in FIG. 14A-B, chronic GL-II-73 treatment also increased maturation, as shown by the increase in doublecortin ("DBX" which may also be referred to as "DCX") labeling in SV129 mice. Fluoxetine treatment was used as a positive control in each experiment. The results demonstrated that the neurogenesis promoting activity of GL-II-73 was similar or close to that of fluoxetine in this model system.

Effects of Chronic Administration of GL-II-73 on Pyramidal Cell Morphology are Long Lasting Table 2 summarizes the results of a quantitative assessment of the morphological properties of Layer II/III pyramidal cells of prefrontal cortex (PFC) between Young, Old, Old-Treatment, and Old-washout groups. As noted above, mice assigned to the "Young" group were 2 months of age at the beginning of the 8-week study and 4 months of age at time of testing; mice assigned to the "Old" group were 22 months of age at beginning of study, 24 months of age at time of testing; mice assigned to the "Old-Treatment" group were the same age as the "Old" group and received GL-II-73 in their drinking water for 8 weeks prior to evaluation; and mice assigned to the "Old-washout" group were the same age and treatment as the "Old-Treatment" group except that the GL-II-73 was removed for a 1 week "wash-out" period prior to evaluation. Differences in total dendritic lengths, overall spine counts, and overall spine density between groups were determined via ANOVA analysis.

TABLE 2

Summary of morphological analysis of PFC pyramidal cells between groups.

| Brain ID, treatment group | # Samples | Total segments | Total lengths (microns) | Total spine counts | Overall spinal density |
|---|---|---|---|---|---|
| Young, water | 4 | 1245 | 61246 | 76772 | 1.25 |
| Old, water | 4 | 1225 | 51566 | 47052 | 0.91 |
| Old, Treatment | 4 | 1180 | 58395 | 64863 | 1.11 |
| Old, Washout | 4 | 1253 | 59414 | 69305 | 1.17 |
| Total | 16 | 4903 | 230621 | 257992 | 1.11 |

Figure 15A:
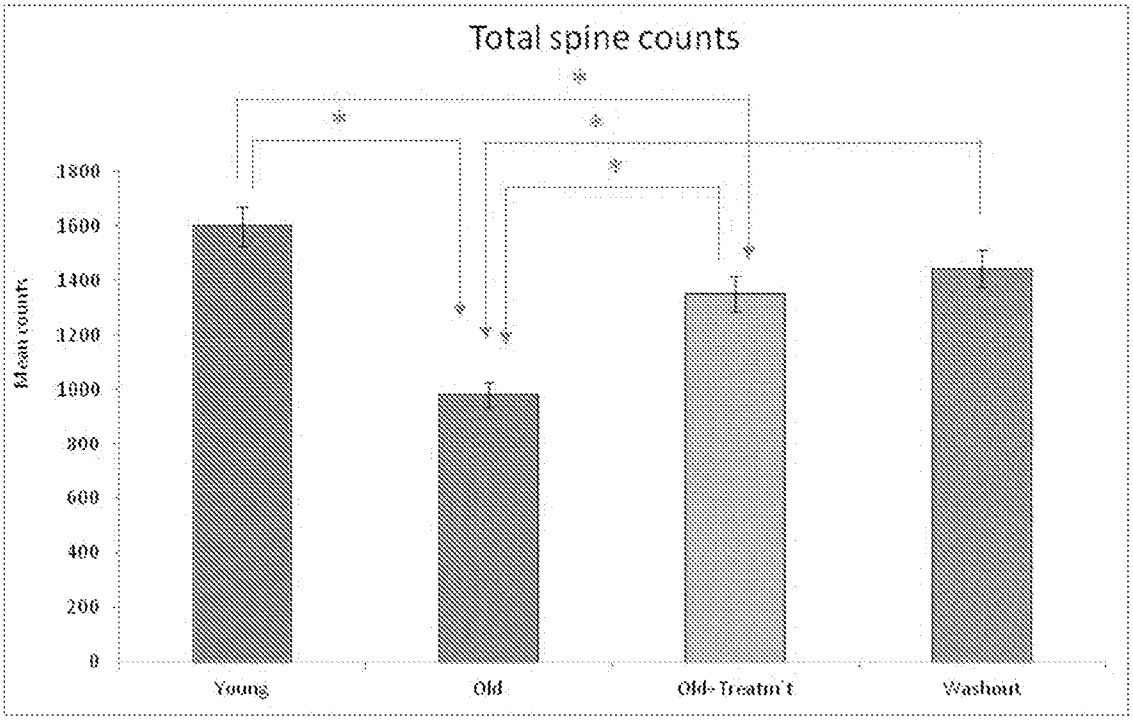
FIG. 15A-B: Comparison of total spine counts of PFC pyramidal cells between groups. (A) Total spine counts in Young, Old, Treatment, and Washout groups; (B) total spine counts broken down into Basal and Apical dendrites for each group.
Figure 15B:
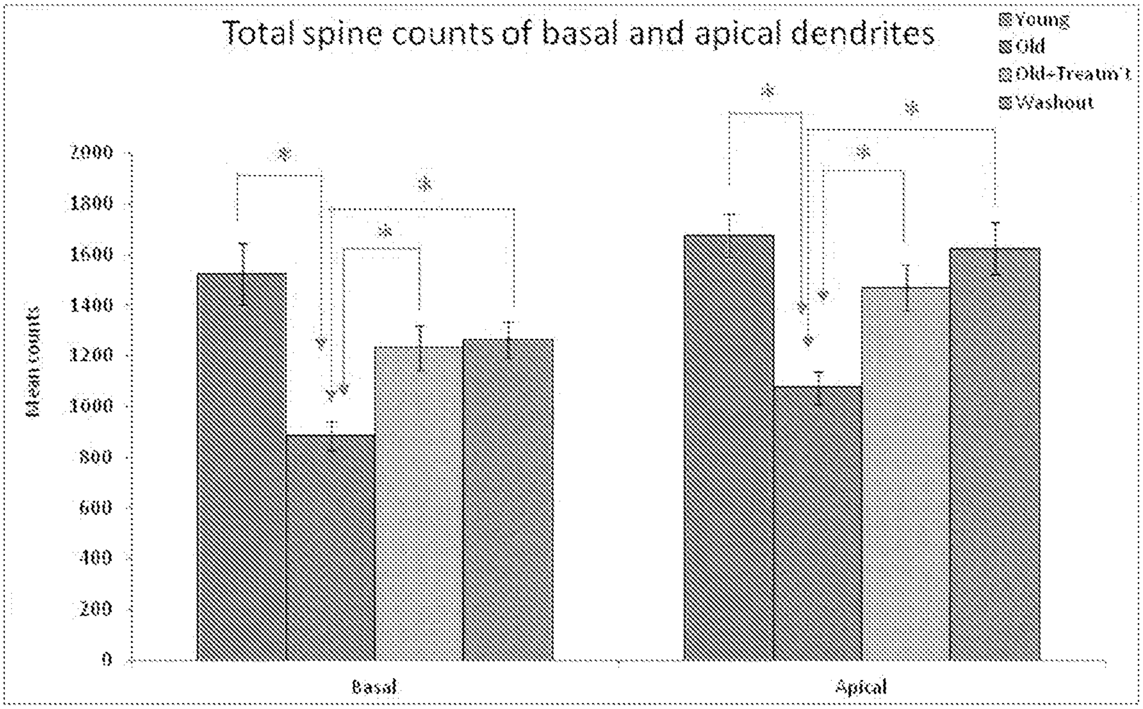

As shown in FIG. 15, total spine counts of PFC pyramidal cells were significantly different between both treatment and washout groups compared to untreated old mice. In comparison with Young mice, there was a significant reduction in total spine counts of Old and Old+Treatment mice, respectively (FIG. 15A, op<0.05). Also, both Old+Treatment and Washout mice exhibited more spine counts than Old mice, respectively (p<0.05). Note that both Young and the two treated groups showed higher spine counts than Old mice (p>0.05). In the break-down analysis, Young, Treatment, and Washout groups all exhibited higher spine counts of both basal (FIG. 15B-left, p<0.05) and apical (FIG. 15B-right, p<0.05) dendrites compared to Old mice.

Figure 16A:
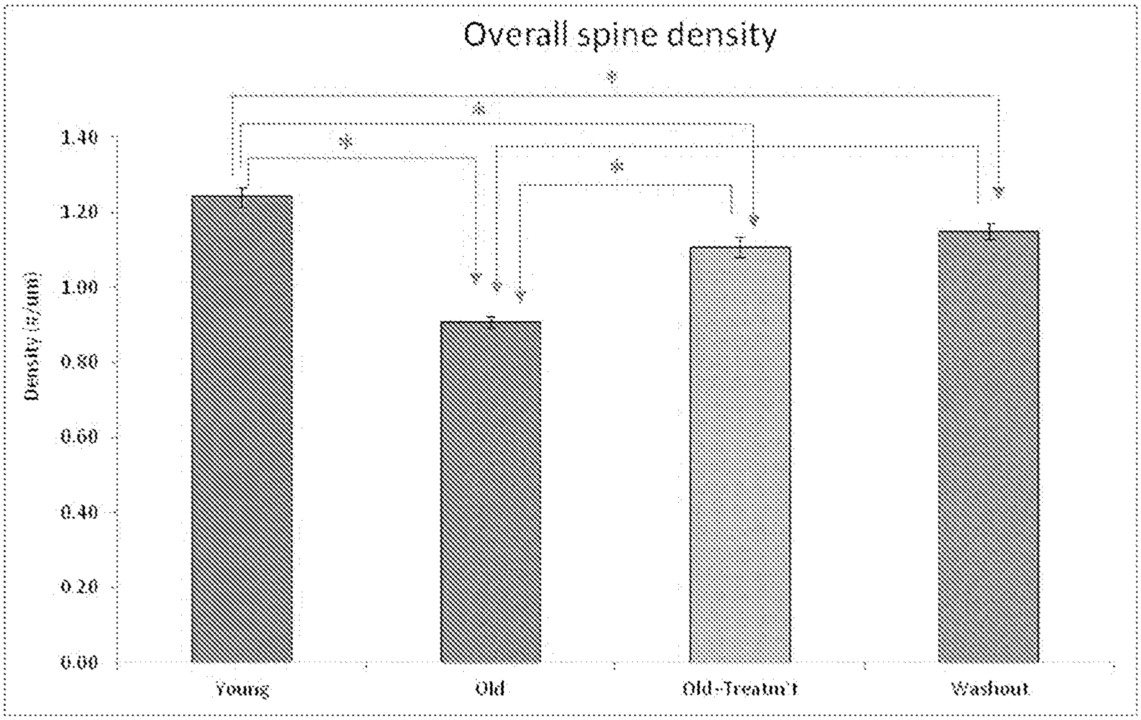
FIG. 16A-B: Comparison of overall spine density of PFC pyramidal cells between groups. (A) Total overall spine density in Young, Old, Treatment, and Washout groups; (B) overall spine density broken down into Basal and Apical dendrites for each group.
Figure 16B:
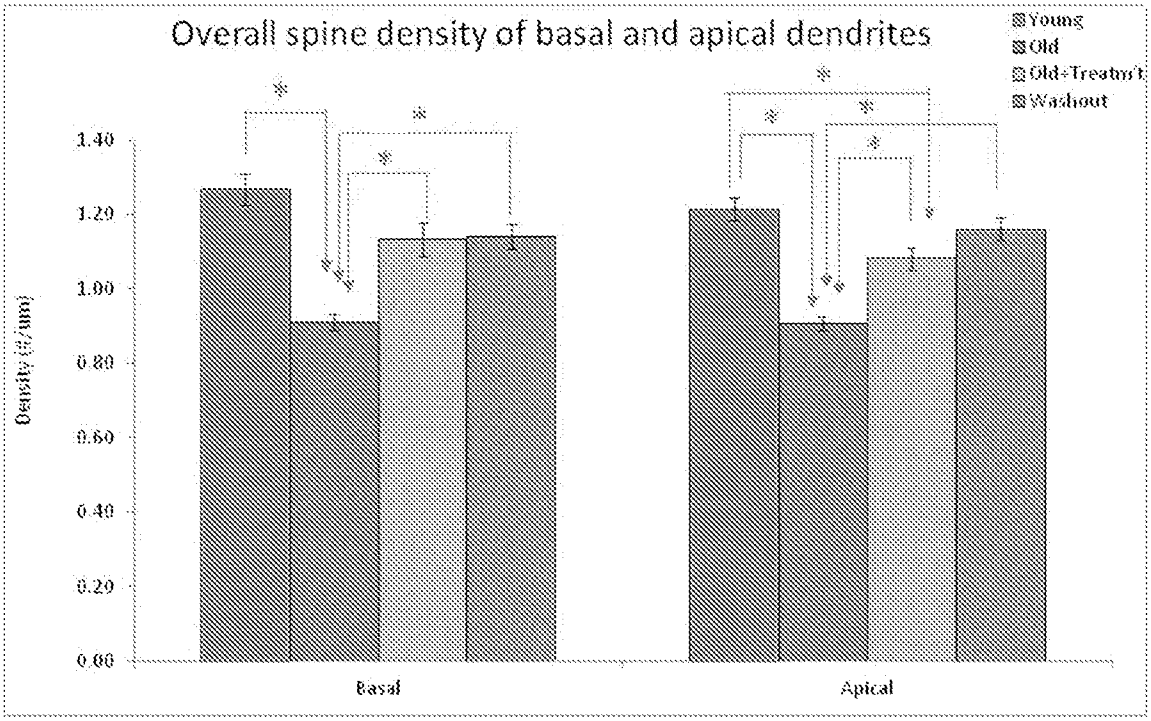

As shown in FIG. 16, overall spine density of PFC pyramidal cells was also significantly different between both the Treatment and Washout groups compared to untreated Old mice. In comparison with Young mice, all aged mice (Old, Old+Treatment and Washout) exhibited a lower overall spine density, respectively (FIG. 16A, p<0.05). Also, both Old+Treatment and Washout mice exhibited a higher spine density than Old mice, respectively (p<0.05). In the break-down analysis, Old mice showed a significant decrease of spine density in the basal dendrite as compared to Young, Old+Treatment and Washout mice, respectively (FIG. 16B-left, p<0.05). Similarly, in the apical dendrites, Old mice exhibited a lower spine density than Young, Old+Treatment and Washout mice, respectively (FIG. 16B-right, p<0.05). Also, Young showed a higher spine density than Old+Treatment but not Washout mice (p<0.05). Note that there was no difference in spine density between Old+Treatment and Washout mice (p>0.05).

Figure 17A:
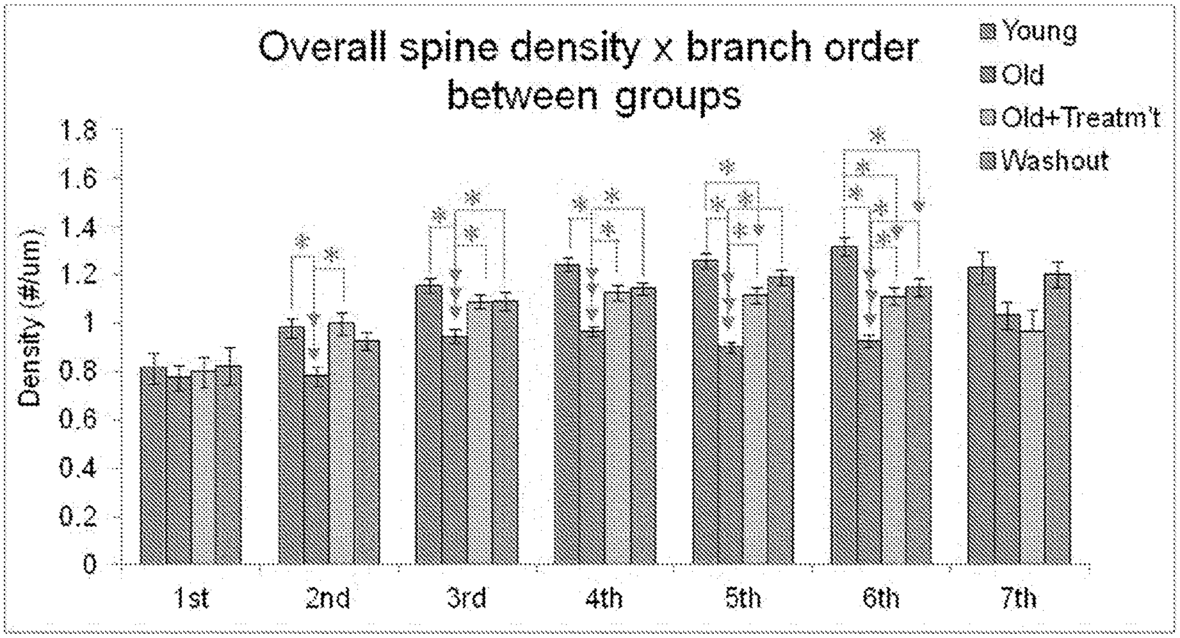
FIG. 17A-C: Comparison of PFC pyramidal cell spine density versus branch order between groups. (A) Overall spine density versus branch order in Young, Old, Treatment, and Washout groups; Panels B-C, overall spine density versus branch order broken down into Basal (B) and Apical (C) dendrites for each group.
Figure 17B:
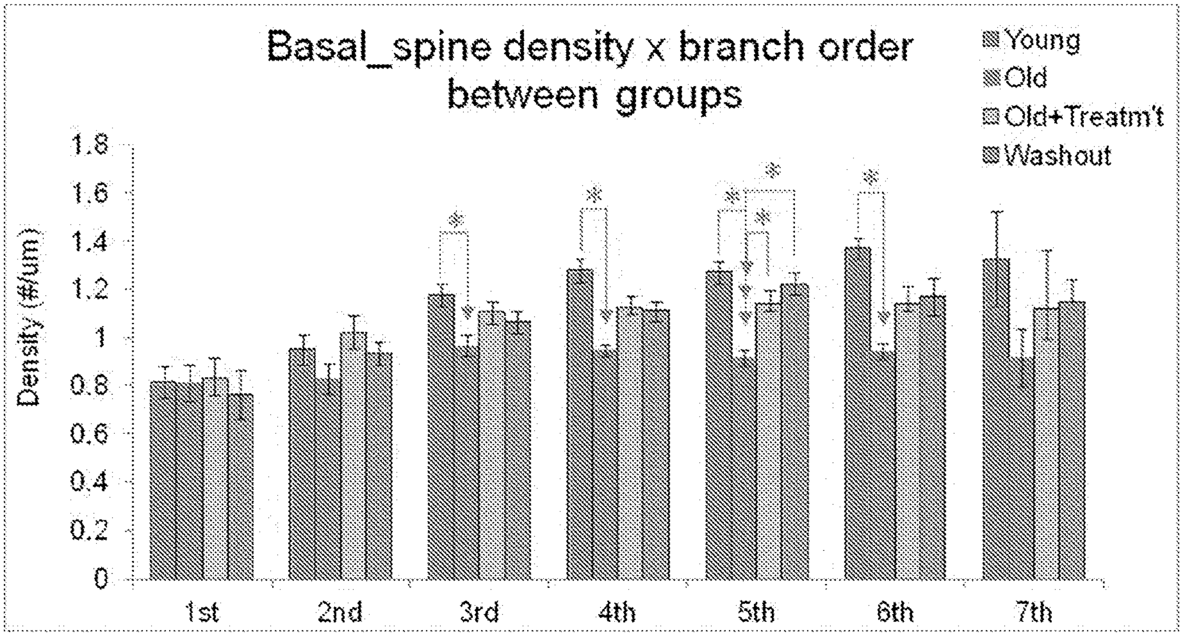
Figure 17C:
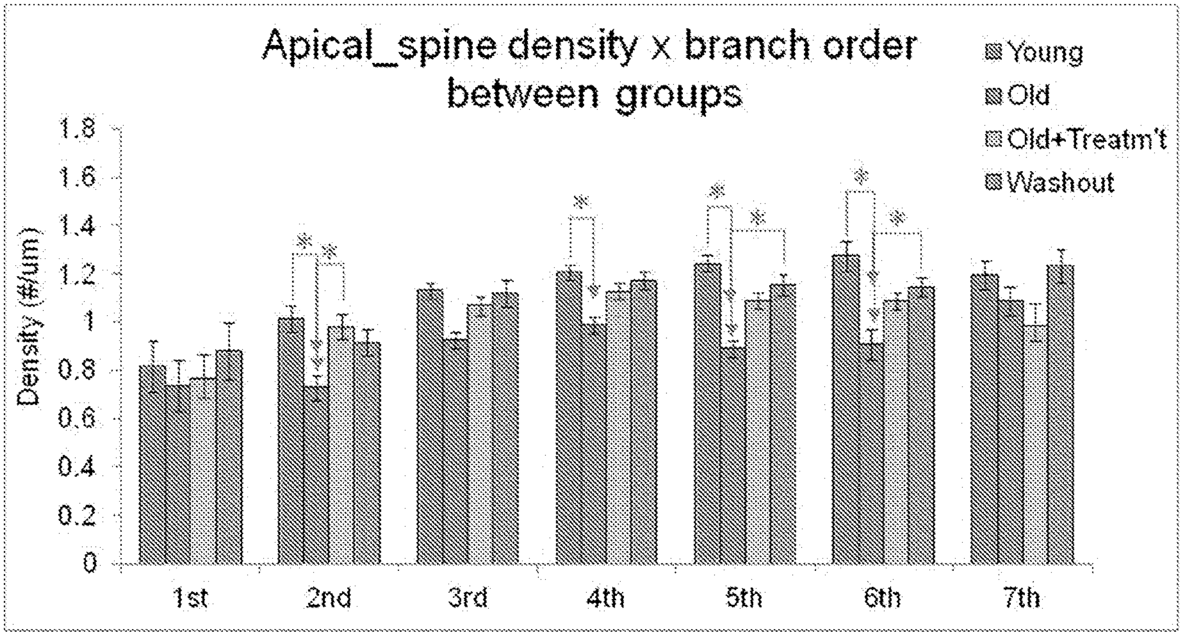

FIG. 17 shows a comparison of PFC pyramidal cell spine density versus branch orders of pyramidal cells between groups. While ANOVA tests showed a significant difference in the spine density between groups (p<0.05), post-hoc tests showed that Young mice had a higher spine density at most branch orders (the 2nd to 6th) than Old mice, at the 5th and 6th branch order than Old+Treatment mice, and at the 6th branch order than Washout mice, respectively (FIG. 17A, p<0.05). Also, comparing with Old mice, both Old+Treatment and Washout mice showed a higher spine density at the 2nd to 6th and 3rd to 6th branch orders, respectively (p<0.05). In the break-down analysis, Young mice showed a higher density at the 3rd to 6th branch orders of basal dendrites than Old mice (FIG. 17B, p<0.05). Note that both treated groups had a higher density at the 5th branch order than Old mice, respectively (p<0.05). In the apical dendrites (FIG. 17C), Young mice showed a higher density at the 2nd and 4th to 6th branch orders than Old mice (p<0.05), whereas Old+Treatment mice showed a higher density at the 2nd branch order than Old mice (p<0.05), and Washout mice had a higher spine density at the 5th to 6th branch orders than Old mice, respectively (p<0.05). Note that no difference was found at most branch orders of basal (FIG. 17B) and apical (FIG. 17C) dendrites between two treated groups, respectively (p>0.05).

Figure 18A:
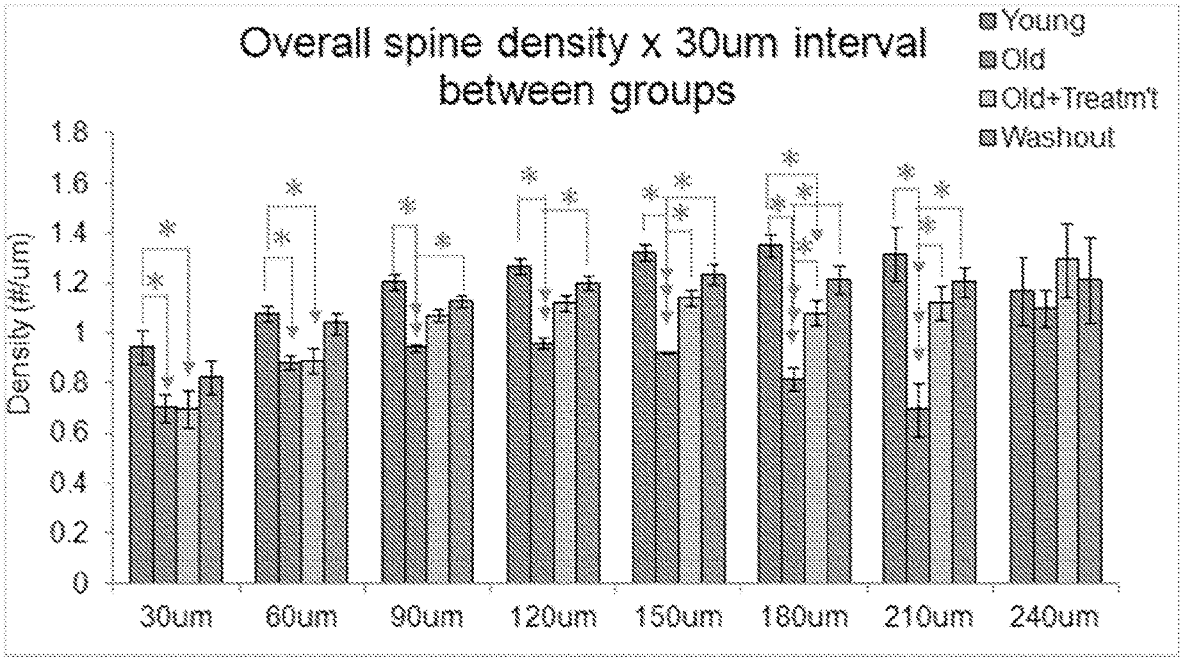
FIG. 18A-C: Comparison of PFC pyramidal cell spine density at 30 micron intervals between groups. (A) Overall spine density in 30 micron intervals from 30 to 240 microns in Young, Old, Treatment, and Washout groups; Panels B-C, overall spine density broken down into Basal (B) and Apical (C) dendrites for each group.
Figure 18B:
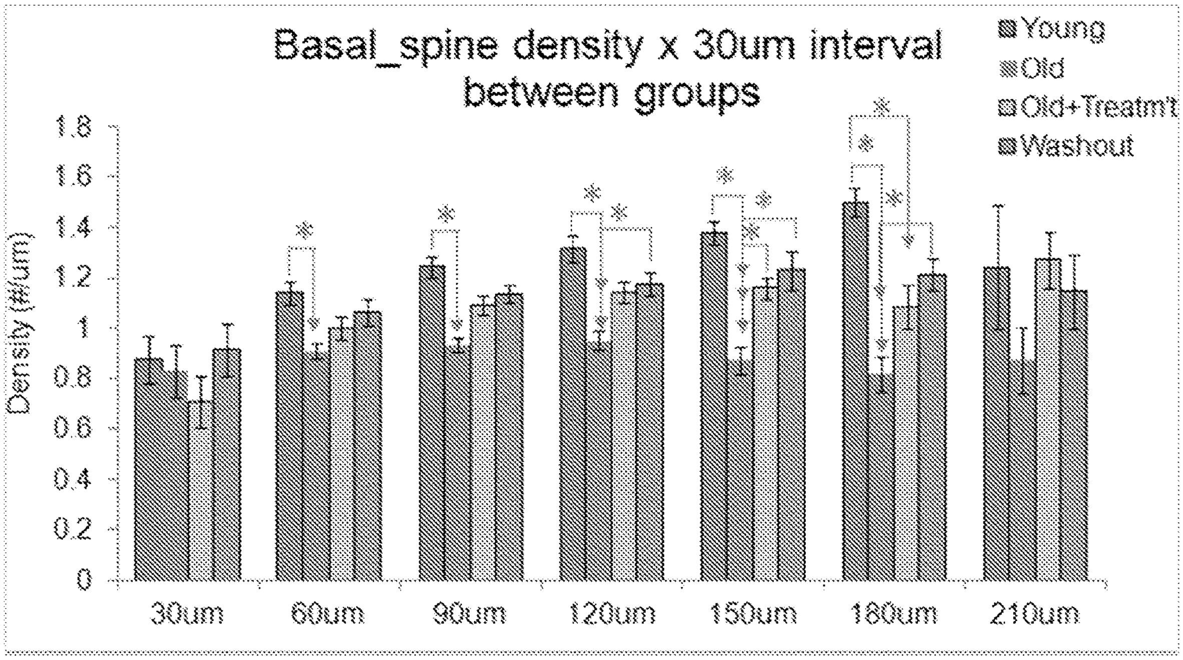
Figure 18C:
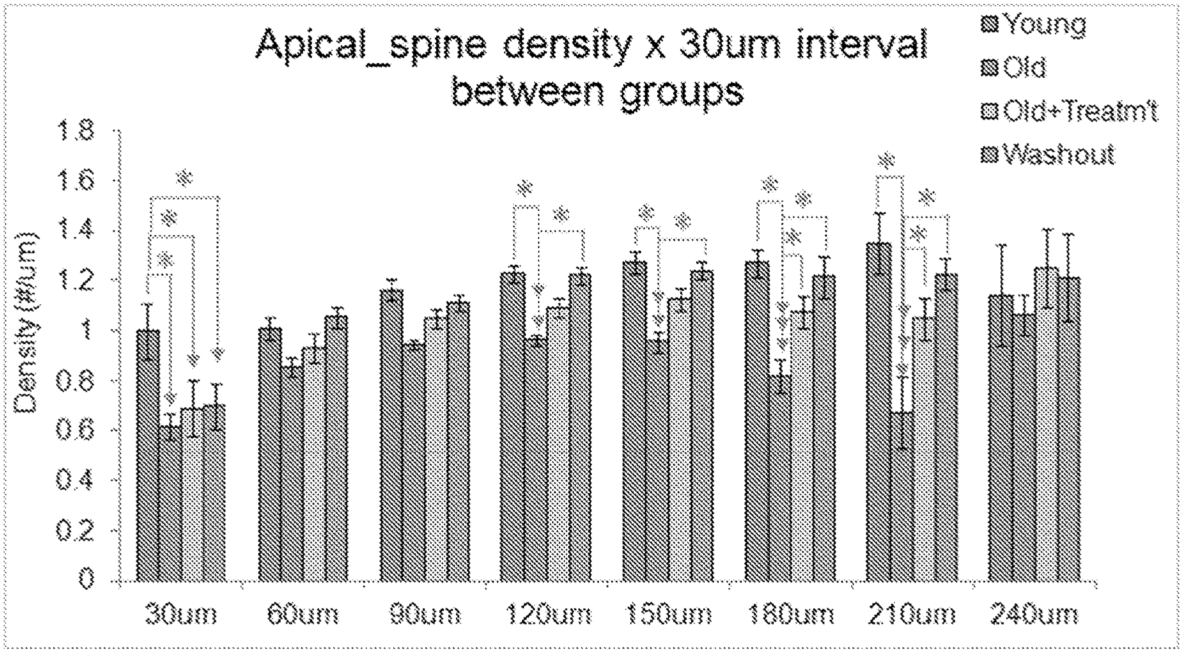

FIG. 18 shows a comparison of PFC pyramidal cell spine density at 30 micron (um) intervals from the soma of pyramidal cells between groups. While ANOVA tests showed a significant difference in the spine density between groups (p<0.05), post-hoc tests showed that Young mice had a higher spine density at most dendritic fields (30 um to 210 um from soma) than Old mice, and at 30 um to 60 um and 180 um from soma than Old+Treatment mice, respectively (FIG. 18A, p<0.05). Also, comparing with Old mice, Old+Treatment mice showed a higher spine density at 150 um to 210 um from soma (p<0.05), whereas Washout mice a higher spine density at 90 um to 210 um from soma, respectively (p<0.05). In the break-down analysis on basal dendrites (FIG. 18B), Young mice showed a higher density at 60 um to 180 um from soma than Old mice (p<0.05), and at 180 um from soma than Old+Treatment mice, whereas Old+Treated mice showed a higher density between 150 um and 180 um from soma, and Washout mice showed a higher density between 120 um and 180 um from the soma than Old mice, respectively (p<0.05). In the apical dendrites (FIG. 18C), Young mice showed a higher density at 30 um and 120 um to 210 um from soma than Old mice (p<0.05) and at 30 um and from soma than Old+Treatment and Washout mice, respectively (p<0.05). Also, compared to Old mice, Old+Treatment mice showed a higher density at 180 um to 210 um from soma (p<0.05), whereas Washout mice had a higher spine density at 120 um to 210 um from soma, respectively (p<0.05). Note that no difference was found between Old+Treatment and Washout mice (p>05).

Generally, these results in PFC pyramidal cells show that all aged groups exhibited a significant reduction in spine density of pyramidal cells as compared to Young mice. Notably, while both Treatment and Washout mice had a higher spine density than Old (untreated) mice, there was no difference in spine density between the two treated groups (Treatment and Washout). In addition, the morphological changes could be attributed to changes in both basal and apical dendrites.

The comparisons of spine density versus branch orders between groups showed that Young mice exhibited a higher spine density at most branch orders ($2^{nd}$ to $6^{th}$) compared to Old mice, and primarily at higher branch orders compared to the two treated groups ($5^{th}$-$6^{th}$ orders of Treatment, and $6^{th}$ order of Washout mice). In addition, both treated groups (Treatment and Washout) had a higher density at the majority of branch orders ($2^{nd}$ to $6^{th}$) compared to the Old group and the changes were found in both basal and apical dendrites. Notably, both treated groups (Treatment and Washout) did not show any significant difference compared with each other in spine density through all dendritic branch orders of pyramidal cells.

In the comparisons of spine density at 30 um intervals from soma of PFC pyramidal cells between groups, Young mice showed a higher density at most dendritic fields compared to the Old group (30 um to 210 um from soma) and the Treatment group (30 um to 60 um and 180 um from soma). Both treated groups (Treatment and Washout) showed a higher spine density compared to the Old group, beginning from the middle half of the dendritic fields (150 um to 210 um from soma of Treatment mice and 90 um to 210 um from soma of Washout mice). There was no difference in spine density between these two treated groups, and in both the morphological changes were found in both basal and apical dendrites.

We also performed the same morphological analyses of pyramidal cells in the CA1 region of the hippocampus for each group. Table 3 shows a summary of the analyses.

TABLE 3

Summary of morphological analysis of CA1 between groups

| Brain ID, treatment group | # Samples | Total segments | Total lengths (microns) | Total spine counts | Overall spinal density |
|---|---|---|---|---|---|
| Young, water | 4 | 1249 | 60695 | 71265 | 1.17 |
| Old, water | 4 | 1235 | 63332 | 56276 | 0.89 |
| Old, Treatment | 4 | 1226 | 60170 | 64468 | 1.07 |
| Old, Washout | 4 | 1266 | 65954 | 72587 | 1.10 |
| Total | 16 | 4976 | 250151 | 264596 | 1.06 |

Figure 19A:
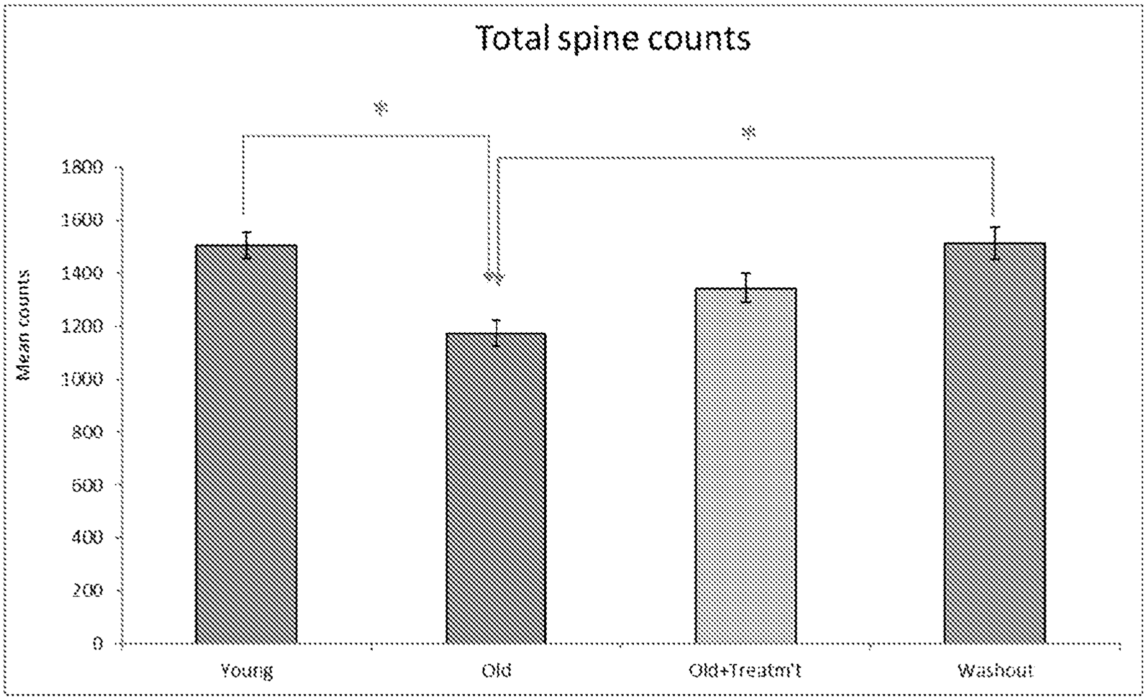
FIG. 19A-B: Comparison of total spine counts of CA1 pyramidal cells between groups. (A) Total spine counts in Young, Old, Treatment, and Washout groups; (B) total spine counts broken down into Basal and Apical dendrites for each group.
Figure 19B:
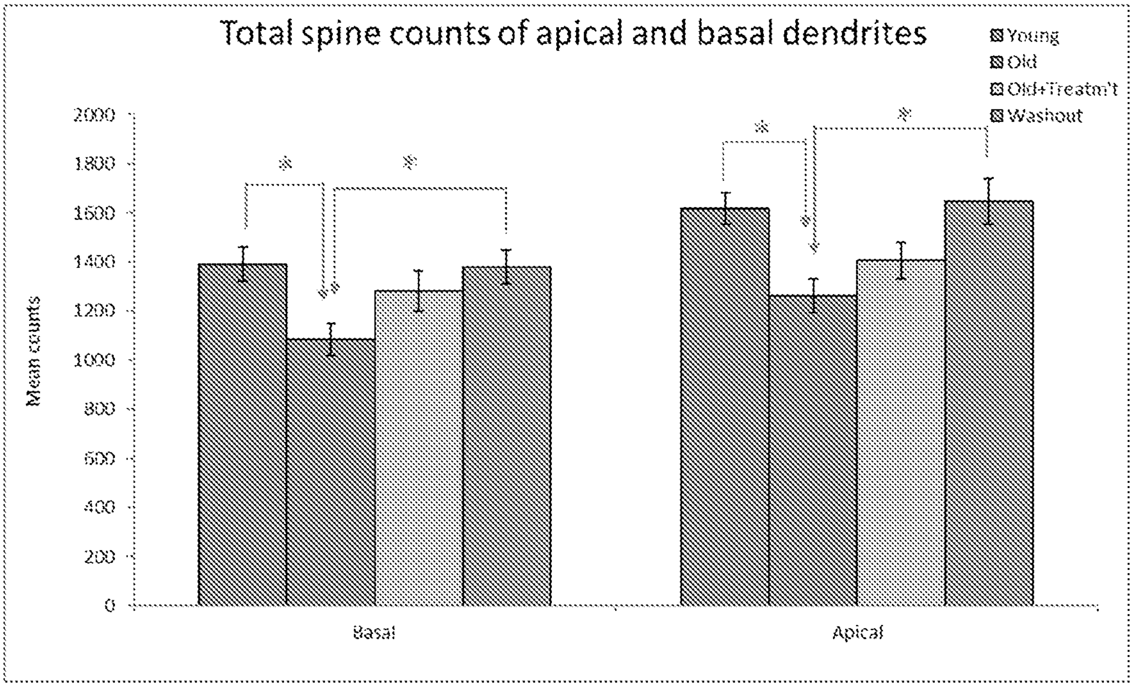

FIG. 19 shows a comparison of total spine counts of CA1 pyramidal cells between groups. In comparison with Young mice, there was a significant reduction in total spine counts of Old mice only (FIG. 19A, op<0.05). It was noted that no difference was found between Young and Old+Treatment as well as Washout mice, respectively (p>0.05). In all aged mice, Washout mice exhibited higher spine counts than Old mice (p<0.05) but showed no difference from Old+Treatment (p>0.05). In the break-down analysis, both Young and Washout mice exhibited higher spine counts of basal dendrites than Old mice, respectively (FIG. 19B-left, p<0.05). Similarly, both Young and Washout mice exhibited higher spine counts of apical dendrites than Old mice, respectively (FIG. 19B-right, p<0.05). Note that there was no difference in total spine counts of both basal and apical dendrites between Young and Old+Treatment as well as Washout mice, respectively (p>0.05).

Figure 20A:
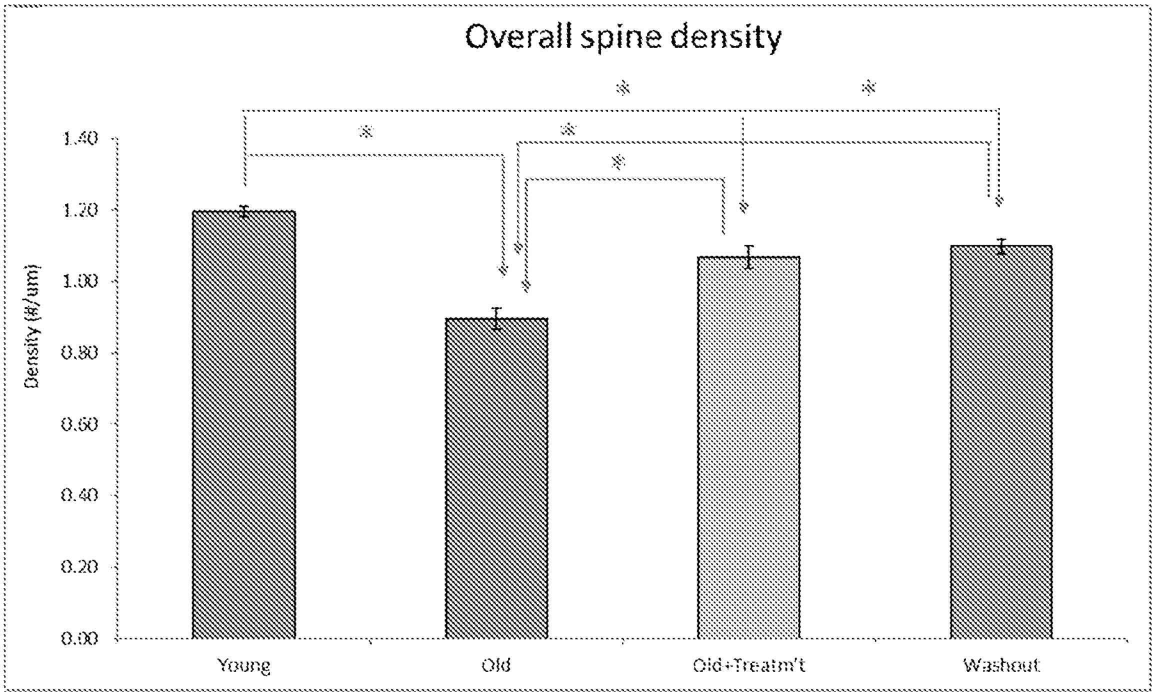
FIG. 20A-B: Comparison of overall spine density of CA1 pyramidal cells between groups. (A) Total overall spine density in Young, Old, Treatment, and Washout groups; (B) overall spine density broken down into Basal and Apical dendrites for each group.
Figure 20B:
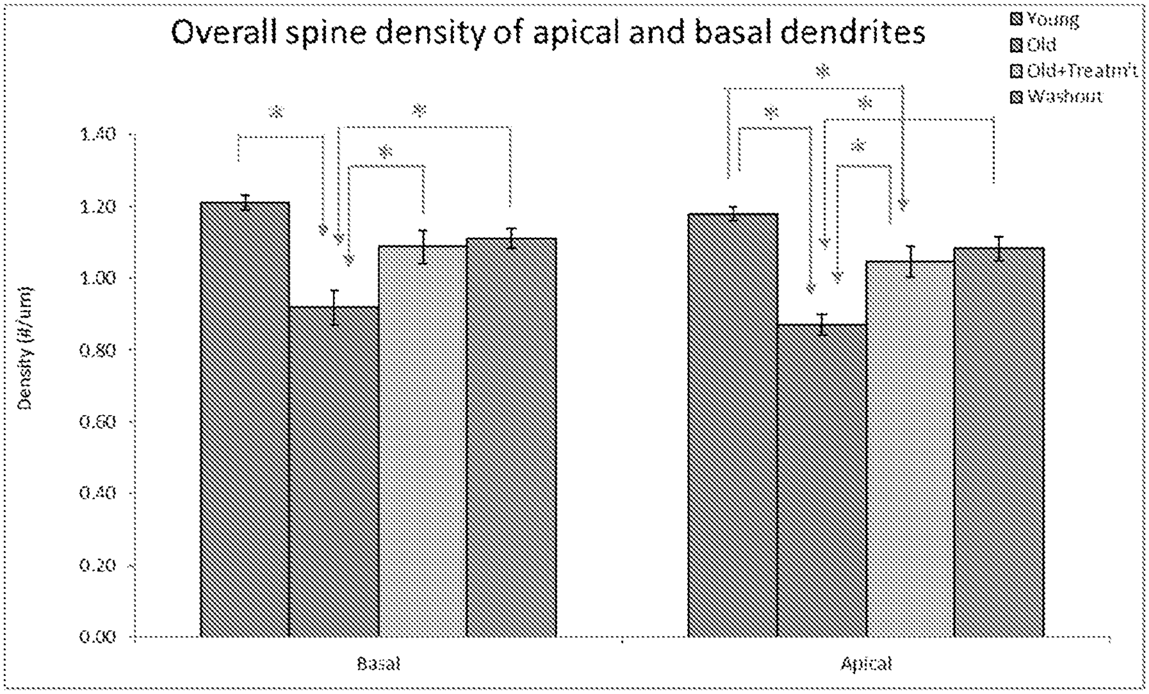

FIG. 20 shows a comparison of overall spine density of CA1 pyramidal cells between groups. In comparison with Young mice, all aged mice (Old, Old+Treatment and Washout) exhibited a lower overall spine density, respectively (FIG. 20A, p<0.05). Also, both Old+Treatment and Washout mice exhibited a higher spine density than Old mice, respectively (p<0.05), whereas no difference was found between both treated groups (Old+Treatment and Washout) (p>0.05). Also, Young mice showed a higher spine density than Old+Treatment mice (p<0.05) but not Washout mice (p>0.05). In the break-down analysis, Old mice showed a significant decrease in the basal dendrite as compared to Young, Old+Treatment and Washout mice, respectively (FIG. 20B-left, p<0.05). Similarly, in the apical dendrites, Old mice exhibited a lower spine density than Young, Old+Treatment and Washout mice, respectively (FIG. 20B-right, p<0.05). Also, there was no difference between Young and Old+Treatment as well as Washout mice, respectively (p>0.05). Moreover, both treated (Old+Treatment and Washout) groups exhibited no significant difference in overall spine density (p>0.05).

Figure 21A:
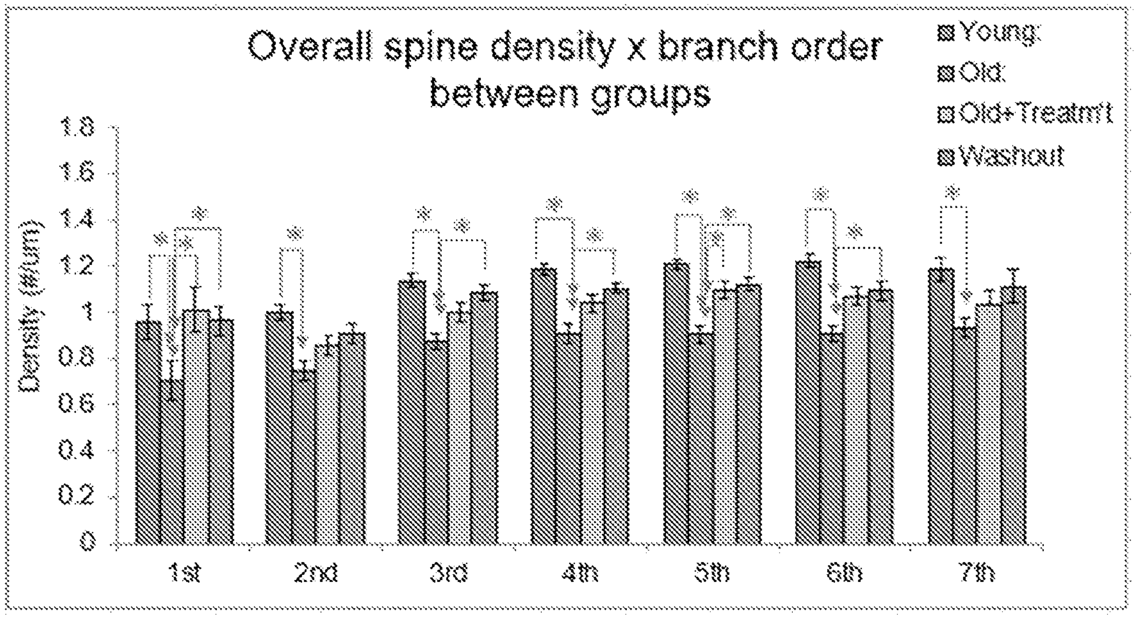
FIG. 21A-C: Comparison of CA1 pyramidal cell spine density versus branch order between groups. (A) Overall spine density versus branch order in Young, Old, Treatment, and Washout groups; Panels B-C, overall spine density versus branch order broken down into Basal (B) and Apical (C) dendrites for each group.
Figure 21B:
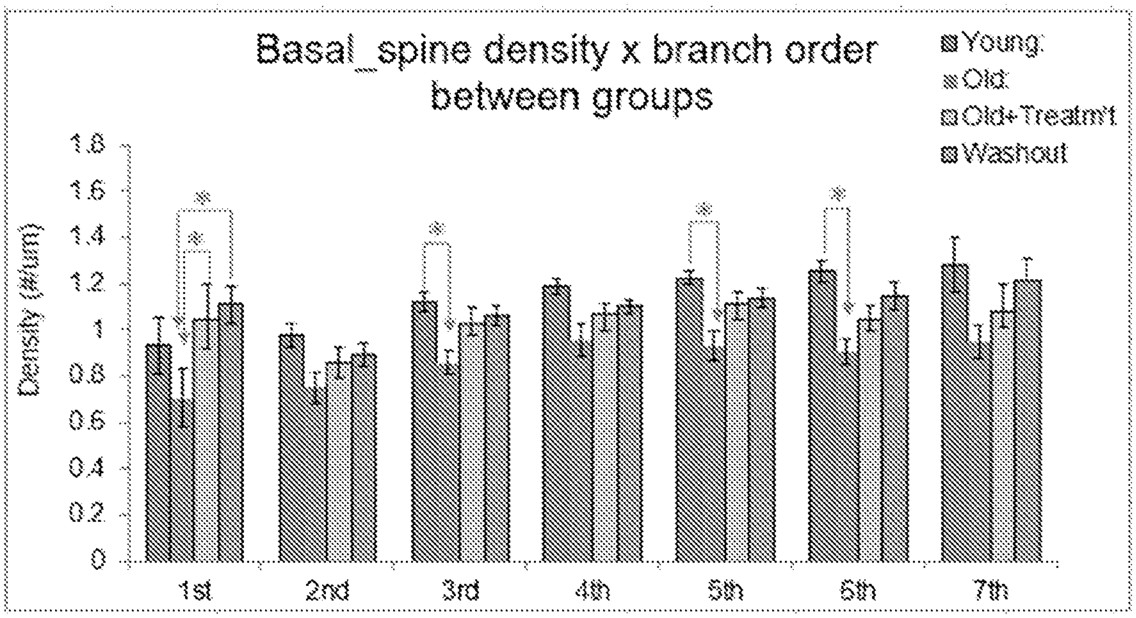
Figure 21C:
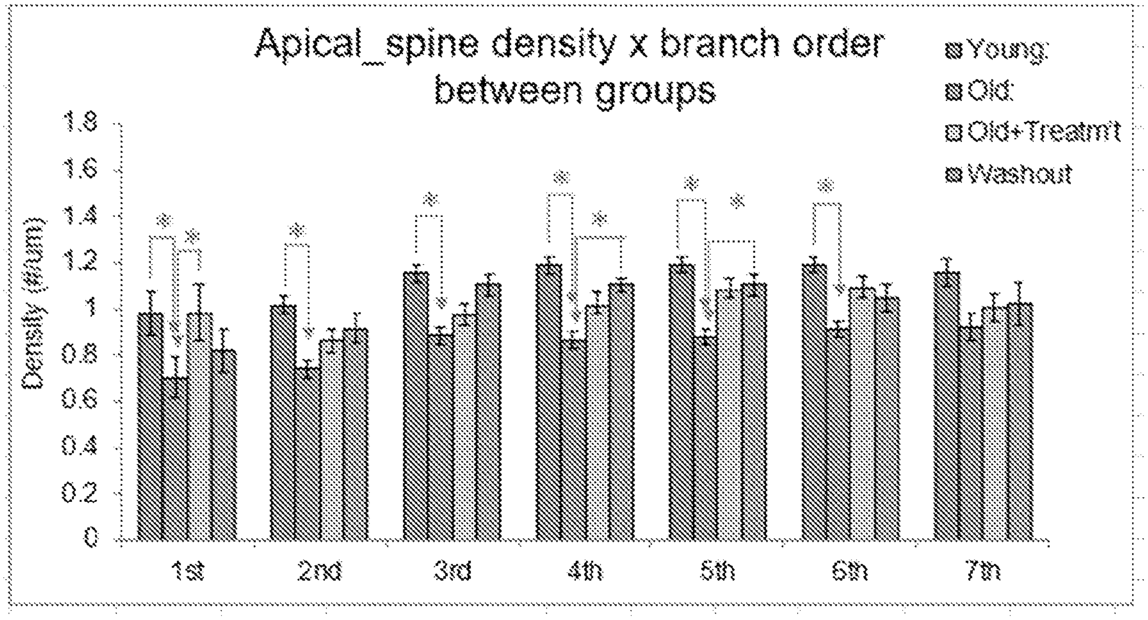

FIG. 21 shows comparisons of spine density versus branch order of CA1 pyramidal cells between groups. While ANOVA tests showed a significant difference in the spine density between groups (p<0.05), post-hoc tests showed that Young mice had a higher spine density at most branch orders (the 1st to 7th) than Old mice only (FIG. 21A, p<0.05). Also, comparing with Old mice, Old+Treatment mice showed a higher spine density at the 1st and 5th branch orders, whereas Washout mice a higher spine density at the 1st and 3rd to 6th), respectively (p<0.05). In the break-down analysis, Young mice showed a higher density at the 3rd, 5th and 6th branch orders of basal dendrites than Old mice (FIG.

21B, $p<0.05$). Note that both treated groups had a higher density at the 1st branch order than Old mice, respectively ($p<0.05$). In the apical dendrites (FIG. 21C), Young mice showed a higher density at the 1st to 6th branch orders than Old mice ($p<0.05$) and showed no difference in most branch orders from both treated groups, respectively ($p>0.05$). Also, Old+Treatment mice showed a higher density at the 1st order than Old mice ($p<0.05$), and Washout mice at the 4th and 5th orders than Old mice, respectively ($p<0.05$). Note that no difference was found at most branch orders of basal (FIG. 21C) and apical (FIG. 21C) dendrites between two treated groups, respectively ($p>0.05$).

Figure 22A:
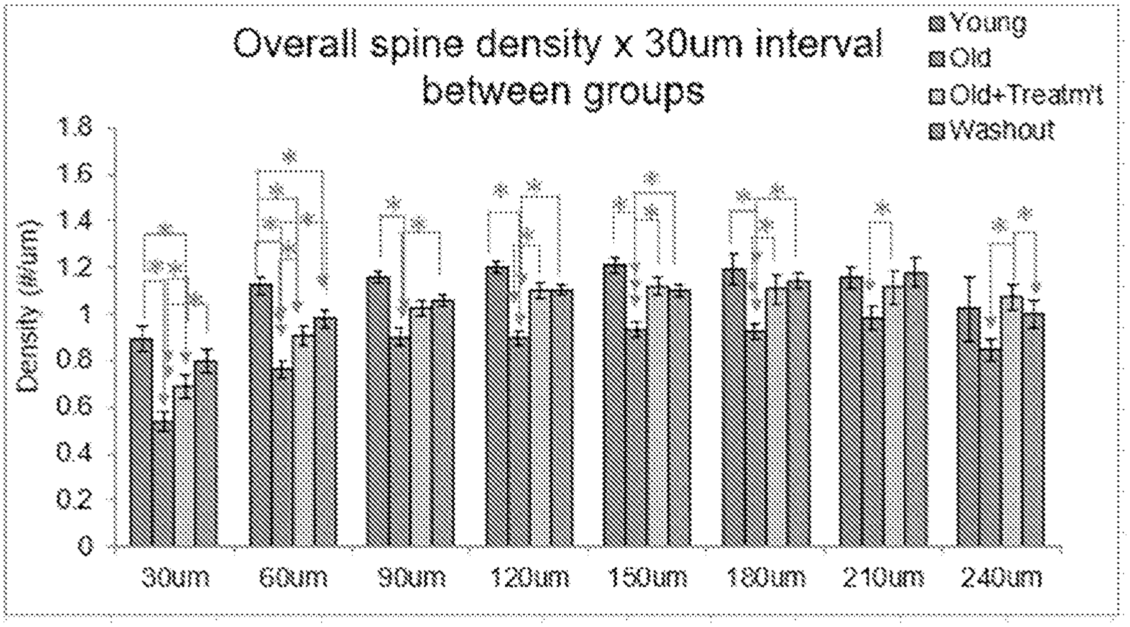
FIG. 22A-C: Comparison of CA1 pyramidal cell spine density at 30 micron intervals between groups. (A) Overall spine density in 30 micron intervals from 30 to 240 microns in Young, Old, Treatment, and Washout groups; Panels B-C, overall spine density broken down into Basal (B) and Apical (C) dendrites for each group.
Figure 22B:
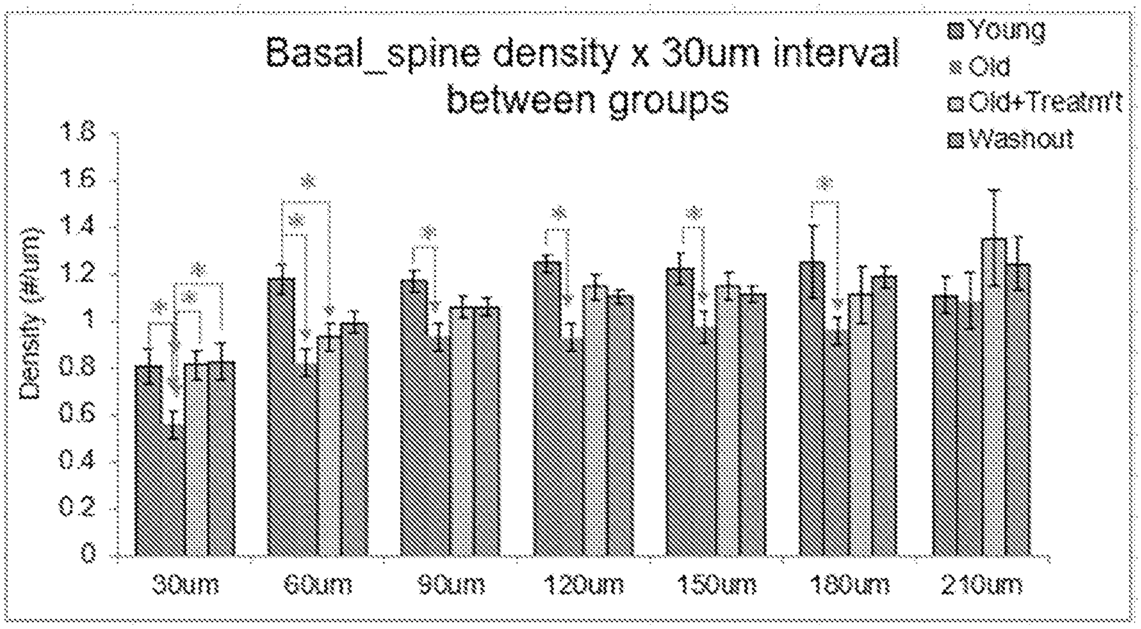
Figure 22C:
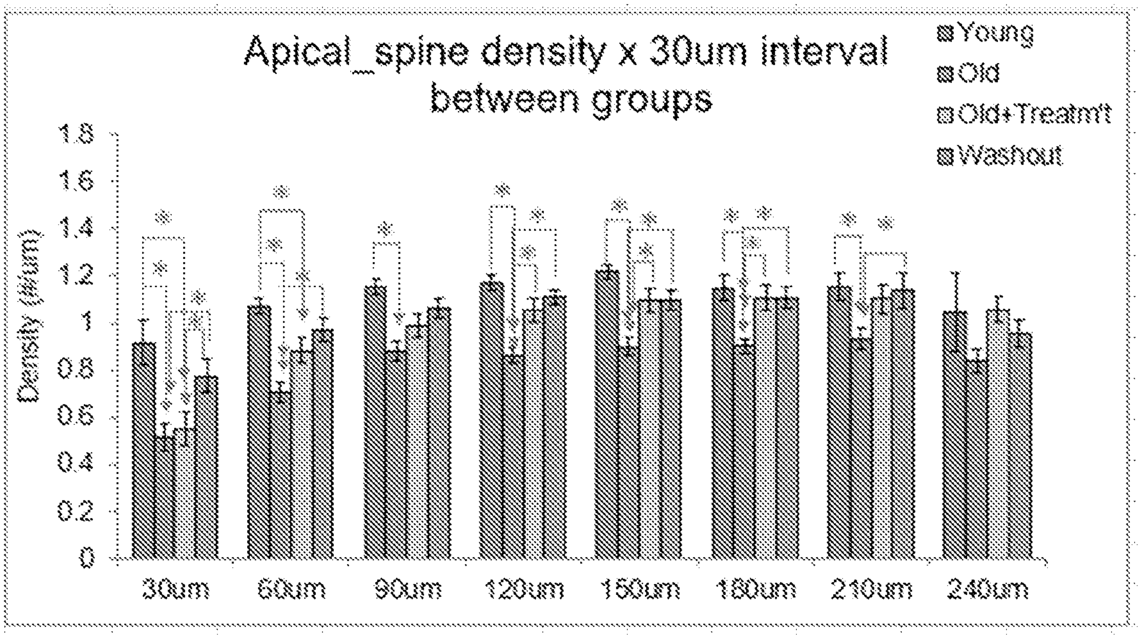

FIG. 22 shows comparisons of spine density at 30 um intervals from the soma of CA1 pyramidal cells between groups. Comparison of spine density×branch orders of pyramidal cells between groups. While ANOVA tests showed a significant difference in the spine density between groups ($p<0.05$), post-hoc tests showed that Young mice had a higher spine density at most dendritic fields (30 um to 180 um) than Old mice, and at 30 um to 60 um from soma than Old+Treatment mice, and at 60 um from soma than Washout mice, respectively (FIG. 22A, $p<0.05$). Also, comparing with Old mice, Old+Treatment mice showed a higher spine density at 30 um to 60 um and 120 um to 240 um from soma ($p<0.05$), whereas Washout mice a higher spine density at 30 um to 180 um from soma, respectively ($p<0.05$). Note a higher density was found at 240 um from soma of Old+Treatment mice than that of Washout mice ($p<0.05$). In the break-down analysis on basal dendrites (FIG. 22B), Young mice showed a higher density at 30 um to 180 um from soma than Old mice ($p<0.05$), and at 60 um from soma than Old+Treatment mice, whereas both treated groups showed a higher density at 30 um from soma than Old mice, respectively ($p<0.05$). In the apical dendrites (FIG. 22C), Young mice showed a higher density at 30 um to 210 um from soma than Old mice ($p<0.05$) and at 30 um to 60 um from soma than Old+Treatment mice, respectively ($p>0.05$). Also, Old+Treatment mice showed a higher density at 120 um to 180 um from soma than Old mice ($p<0.05$), whereas Washout mice had a higher spine density at 30 um to 60 um and 120 um to 210 um from soma than Old mice, respectively ($p<0.05$). Note that no difference was found at most dendritic fields ($p>0.05$), except for 30 um from soma between two aged groups, in which Washout mice had a higher spine density than Old+Treatment mice ($p<0.05$).

In general, the analyses of CA1 pyramidal cells for all aged groups showed a significant reduction in spine density compared to the group of Young mice. Notably, while both the Treatment and Washout groups showed a higher spine density compared to the Old (untreated) group, there was no difference in spine density between the two treated groups (Treatment and Washout). In addition, the observed morphological changes were attributed to changes in both basal and apical dendrites.

The results described here further show that in comparing the spine density versus branch orders of CA1 pyramidal cells between groups, the Young group showed a higher spine density at most branch orders compared to the aged groups. In addition, both treated groups had a higher density at some branch orders compared to the Old (untreated) group, and these changes were found in both basal and apical dendrites. Notably, the treated groups (Treatment and Washout) did not show any significant differences in spine density through all branch orders of pyramidal cells as compared to each other.

In the comparison of spine density at 30 um intervals from soma of CA1 pyramidal cells between groups, Young mice showed a higher density at most dendritic fields than the aged mice of all three groups, Old, Treatment, and Washout; and the treatment groups (Treatment and Washout) showed a higher density compared to the Old (untreated) group. Importantly, here again there was no evidence of any difference in spine density between the two treated groups (Treatment and Washout) and similar changes were found in both basal and apical dendrites.

Figure 23:
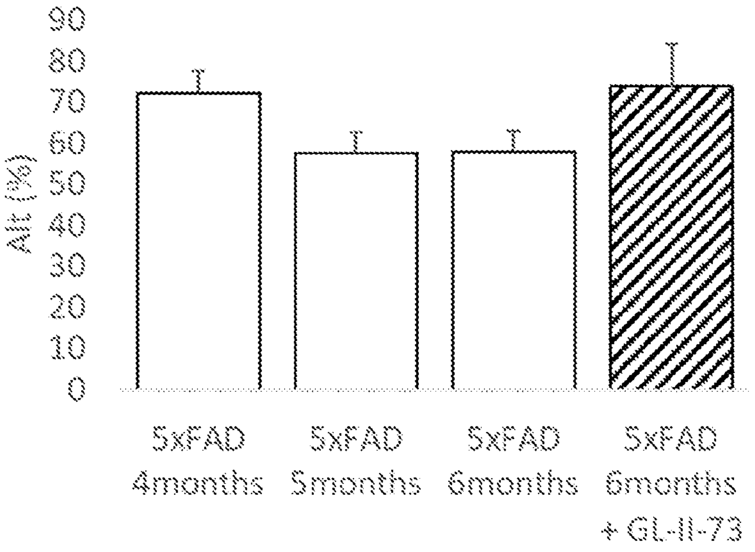
FIG. 23: Alternation performance as percentage in heterozygous 5×FAD mice at 4, 5, and 6 months of age untreated (open bars), and at 6 months of age treated with GL-II-73 (10 mg/kg) (hatched bar).

A pilot study was performed in the 5×FAD mouse Alzheimer's disease model system using 15 heterozygous animals tested from the age of 4 to 6 months. The same animals were tested monthly for spontaneous alternation in the Y-Maze test. When they reached the age of 6 months, 50% of the animals were injected i.p. with vehicle or with GL-II-73 (10 mg/kg). FIG. 23 shows the results of the animals' performance in the test. These data show a gradual decrease of alternation performance with age in the 5×FAD mice, although not reaching statistical significance due to the small sample size (ANOVA $p>0.1$). The data also show a reversal of this decrease in alternation performance in the GL-II-73 treated group, although also not reaching statistical significance due to the small sample size. Additional studies are being conducted to confirm these results of a pro-cognitive effect of GL-II-73 in 5×FAD mice when given acutely.

DISCUSSION

Here we demonstrate that chronic administration of GL-II-73 in old mice is effective to improve age-related cognitive decline, as measured by a reduction in the percentage of alternation during the Y maze test. We also show that treatment with GL-II-73 prevented the age-related decreases in dendritic length, number of spines, and spine density in the pyramidal neurons of both the pre-frontal cortex (PFC) and the CA1 pyramidal cells of the hippocampus. Finally, we demonstrated that the effects of GL-II-73 treatment on spine morphology and density of the PFC pyramidal cells and the CA1 pyramidal cells of the hippocampus was long-lasting Notably, chronic administration of GL-II-73 prevented age-related morphological changes only on the apical segment of the dendrites in the both the pre-frontal cortex and hippocampus. The apical segments are special features corresponding with the specific location of the α5-GABAA receptors which are located on the apical segment of the dendritic tree.

Our results indicate that chronic administration of GL-II-73 enhances the activity of α5-GABAA receptors at the apical segment of the dendrites in both the hippocampus and the pre-frontal cortex, fostering the maintenance of synapses that would otherwise lose their functionality and morphology during aging or during the progression of neurodegenerative disease. As both brain regions (PFC and the CA1 region of the hippocampus) are essential for cognitive processes, and are both severely impaired during aging or neurodegenerative disorders, we expect that these effects on morphological shrinkage of dendrites can prevent age-related cognitive impairment and decline as well as neurocognitive decline incident to neurodegenerative disease.

In addition, we have shown that chronic treatment with GL-II-73 stimulates neurogenesis in the SV129 mouse model. Specifically, we found that treatment increased neuronal cell proliferation, the survival of the new cells, and their maturation. These results further indicate that GL-II-73 can be used to compensate for cell loss, potentially associated with cognitive impairment during aging or neurodegenerative disease.

We are further testing these predictions in ongoing and future studies using mouse models of normal aging and Alzheimer's disease. We have confirmed cognitive decline in 5×FAD mice until the age of 6 months, and preliminary results suggest a pro-cognitive effect of GL-II-73 when given acutely at that age. We expect that GL-II-73 will alleviate cognitive decline and reduce dendritic shrinkage in normal aging and early stage Alzheimer's disease models, but may have reduced efficacy in later stage disease due to putative interactions with disease pathologies, highlighting the use of GL-II-73 as a prophylactic agent for preventing cognitive impairment and neurocognitive decline.

Methods

Animals: For the experiments described above, young (n=11, age 2 months) and old male mice (N=23) were purchased from Charles River. Old mice were obtained at the age of 9-10 months and were kept in the animal facility until they reached the age of 22 months. Young mice (2 months old) were purchased when old mice had already reached the age of 22 months. All animals were single housed. Experiments were performed on mice aged 2 months ("young") or 22 months ("old") at the beginning of the experimental protocol. The second set of experiments with the Washout group included 8 young mice and 22 old mice. Old mice were split into 3 groups of 7-8 between "Old", "Old-treated" and "Old-Washout". Finally, the pilot with the 5×FAD mice was performed with 15 heterozygote 5×FAD mice, bred in the animal facility of the Centre for Addiction and Mental Health, Toronto (ON, Canada).

Drug preparation and administration: The compound GL-II-73 was administered in the drinking water for 8 weeks, and made fresh every other day to prevent any deterioration of the compound in the water at room temperature. The solution was prepared at 30 mg/kg for an estimated volume of 8 ml/mouse/day, based on previous calculations. For the pilot study in the 5×FAD mouse model, the compound GL-II-73 was prepared for intra peritoneal injection only, at a dose of 10 mg/kg. Vehicle solution was made of 85% distilled water, 14% propylene glycol and 1% tween-80.

Behavioral testing (general): For all behavioral tests, young and old mice are first habituated to the experimenter following a handling protocol. Handling reduces acute stress when the experimenter is operating with the animal, ultimately reducing variability within a group. Following this protocol, animals are manipulated by the experimenter for 5 minutes per day, letting them habituate to be picked up from the cage, to contact with gloves and to being placed in the hand of the experimenter. After 3 days of the handling procedure, the compound GL-II-73 is administered to a group of old mice (N=8) in the drinking water, the "treatment" group, while another group of old mice (N=12) and the young mice (N=11) receive only tap water. Behavioral testing is carried out after 8 weeks of treatment with GL-II-73, or water-only.

Spontaneous alternation in the Y-Maze: Mice were tested in a Y maze test as an assessment of working memory. The apparatus was a black plastic Y-maze with 3 arms, 26 cm long, 8 cm wide with sidewalls 13 cm high and all separated by 120°; each arm having a sliding door. The protocol used was a modified version of the one described in Vandesquille et al. (2011): S 18986 reverses spatial working memory impairments in aged mice: comparison with memantine. Psychopharmacology. 215:709-720. Briefly, mice were first habituated to the apparatus and to distal cues during 2 consecutive days over a 10 min free exploration session. The following day, animals performed a training session consisting of seven successive trials where they have to alternate between the 2 goal arms with an inter trial interval (ITI) of 30 sec. The same general procedure used in the training session was implemented 24 h later, except that the ITI was lengthened to 60 s. To dissociate memory deficits from an eventual progressive loss of motivation, an 8th trial was added to the series which was separated from the 7th trial by a shorter ITI (5 s). All animals failing to alternate at the 8th trial were excluded from the analysis. The alternation rate was calculated and was expressed as a percentage:

$$\text{Alternation rate} = \frac{\text{Alternation}}{\text{Maximum alternation possible}} \times 100.$$

The percentage of alternation during the entire task was considered as an index of working memory performance (50% of alternation corresponding to a random alternation rate).

Brain collection and Golgi staining: Twenty-four hours after the completion of the behavioral testing, mice were euthanized using cervical dislocation. Brains were carefully collected from the skull, rinsed with MilliQ water and immersed in the Golgi staining solution provided by Neurodigitech (San Diego, CA). Six hours after the beginning of the incubation, the solution was changed to provide fresh solution. Then brains were left incubating for 14 days at room temperature, in the dark. For better results, vials containing the brains were gently swirled 3 times a week. After the incubation period, the staining solution was discarded and replaced by a storage solution and brains (n=4 per group) were shipped to Neurodigitech for morphological analysis.

Slice preparation: Brains were cut at 40 μm thickness using a cryostat and mounted on glass slides. The slides included serial coronal sections that covered the anterior-to-posterior axis of the brain. The sampling of ROIs included the basal and apical dendrites of pyramidal cells in Layers II/III of PFC. The ROIs were then chosen and analyzed using a stereology-based software, called NeuroLucida, v10 (Microbrightfield, VT), installed on a Dell PC workstation that controlled Zeiss Axioplan 2 image microscope with Optronics MicroFire CCD camera (1600×1200) digital camera, motorized X, Y, and Z-focus for high-resolution image acquisition and digital quantitation.

Sample selection criteria: The sampling process was conducted as follows: The investigators first 1) previewed the entire rostro-caudal axis of ROIs, under low-mag Zeiss objectives (10× and 20×), 2), compared and located those with the least truncations of distal dendrites as possible under high-mag Zeiss objectives (40× and 63×), 3), and then 4) used a Zeiss 100× objective with immersion oil to perform 3D dendritic reconstruction, followed by counting of the spines throughout the entire dendritic trees. The criteria for selecting candidate neurons for analysis were based on i) visualization of a completely filled soma with no overlap of neighboring soma and completely filled dendrites, ii) the tapering of most distal dendrites; iii) the visualization of the complete 3-D profile of dendritic trees using the 3-D display of imaging software. Neurons with incomplete impregnation and/or neurons with truncations due to the plane of sectioning were not collected. Moreover, cells with dendrites labeled retrogradedly by impregnation in the surrounding neuropil were excluded.

With the systematic registration and digital monitoring, the software was able to accurately record every step of the tracing/contouring and generate a 3D reconstructed dendritic morphology for subsequent spine counting. Automatic navigation of the digital probes with registered x-y-z coordinates of each 2D image stack was able to create a complete 3D digital profile for the dendrograms, spine density and Sholl analysis (see below).

Spine Sampling Criteria & Quantitative Analysis

Spine sampling: Only spines orthogonal to the dendritic shaft were readily resolved and included in this analysis, whereas spines protruding above or beneath the dendritic shaft were not sampled (see below). This principle was remained consistent throughout the course of analysis. Also, due to inevitable truncations of most distal ends of the sections and shrinkage after impregnation process and optical limit to resolving most distal dendrites in deep z-axis, under-estimates of the actual dendritic lengths and spine numbers would be expected. The above limitations, however, did not affect the comparison of morphological properties between animals of the current study.

Quantitative analysis: After tracing and spine counting, the raw data were extrapolated and quantitated using NeuroExplorer program (Microbrightfield, VT). In addition, to further investigate the change in spine morphology, Sholl analysis was performed to characterize the spine properties in reference to a series of concentric circles (spheres in 3D) around the soma of the sampled neurons. Within each sphere, various measures were obtained, including 1) Frequency of intersections (or dendritic ramification) and 2) Spine density based on every 30 um interval or concentric circle from the soma (FIG. 10). Note: Frequency of intersections represents the intersections or ramifications of dendritic processes interacting with the concentric rings from the soma of pyramidal cells. After completion, the digital profile of neuron morphology was extrapolated and transported to a multi-panel computer workstation for the quantitative analysis, including the dendrograms, spine counts, and Sholl analyses.

Statistics: Statistical analyses were performed using the Statview software. ANOVAs were used to detect potential difference between groups. If significant, the ANOVA analysis was followed by post-hoc Fisher's PLSD test to identify the origin of the significance.

Alzheimer's Model

For ongoing and future studies using a mouse model of Alzheimer's disease, the 5×FAD mouse line is being used. These mice express high levels of mutant amyloid protein precursor (APP) and presenilin-1 (PSEN1), two genes for which genetic variants confer higher risk for developing Alzheimer's disease. (Oakley H et al. Intraneuronal beta-amyloid aggregates, neurodegeneration, and neuron loss in transgenic mice with five familial Alzheimer's disease mutations: potential factors in amyloid plaque formation. J Neurosci. 2006 Oct. 4;26(40):10129-40. PubMed.). 5×FAD mice display a progressive Aβ pathology, corresponding to prodrome (2 months), early (3-4 months) and late phases (6 months) of Alzheimer's disease. Two pairs of 5×FAD transgenic mice were purchased from Jackson Laboratory and are being bred to generate 40 mice (50% females). The design of the study is depicted in FIG. 23. Half of the mice will be used to assess the effects of GL-II-73 during the early stage of plaque development in the 5×FAD mouse brain (1-3 months of age), and the other half during the late stage (4-6 months of age). Mice will receive GL-II-73 in the drinking water (n=10) or water alone (n=10) from the age of 1 month to the age of 3 months for the early stage analysis. Mice will be tested in the Y maze at 1, 2 and 3 months, and then euthanized for downstream analysis (Golgi Staining) at the age of 3 months. A similar design will be used to assess the effect of chronic GL-II-73 administration during the late stage of plaque accumulation, with GL-II-73 being given between 4 and 6 months of age and brains being harvested at the age of 6 months.

EQUIVALENTS

Those skilled in the art will recognize or be able to ascertain using no more than routine experimentation, many equivalents to the specific embodiments of the invention described herein. Such equivalents are intended to be encompassed by the following claims.

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. A method for delaying the onset of one or more symptoms of cognitive impairment or neurocognitive decline by stimulating neuronal growth in a subject in need thereof, the method comprising chronically administering to the subject a pharmaceutical composition comprising an alpha5-GABAA receptor agonist, wherein the subject is asymptomatic or undiagnosed prior to administering the agonist, wherein the agonist is administered to the subject for a period of months or years, and wherein the agonist is 8-ethynyl-6-(2-fluorophenyl)-N,N,4-trimethyl-4H-benzo[f]imidazo[1,5-a][1,4]diazepine-3-carboxamide, or a pharmaceutically acceptable salt thereof.

2. The method of claim 1, wherein the subject in need is one who is at risk of developing a neurodegenerative disease or disorder.

3. The method of claim 2, wherein the neurodegenerative disease or disorder is selected from Alzheimer's disease, amyotrophic lateral sclerosis, multiple sclerosis, Parkinson's disease, Huntington's disease, and frontotemporal degeneration.

4. The method of claim 2, wherein the neurodegenerative disease or disorder is Alzheimer's disease.

5. The method of claim 2, wherein the subject has a genetic predisposition to the neurodegenerative disease or disorder.

6. The method of claim 2, wherein the method further comprises a step of assaying, ex vivo, a biological sample from the subject for the presence of a genetic marker or biomarker indicative of increased risk of developing a neurodegenerative disease or disorder.

7. The method of claim 1, wherein the subject in need is one who is at risk of cognitive impairment due to chronic stress.

8. The method of claim 1, wherein the subject in need is one who is at risk of cognitive impairment due to age.

9. The method of claim 8, wherein the subject is 50 years of age or older.

10. The method of claim 1, wherein the pharmaceutical composition is in the form of a dermal patch or nasal spray.

11. The method of claim 1, wherein the agonist is (R)-8-ethynyl-6-(2-fluorophenyl)-N,N,4-trimethyl-4H-benzo[f]imidazo[1,5-a][1,4]diazepine-3-carboxamide, or a racemic mixture that is at least 80% R enantiomer.

12. The method of claim 1, wherein the agonist is (S)-8-ethynyl-6-(2-fluorophenyl)-N,N,4-trimethyl-4H-benzo[f]imidazo[1,5-a][1,4]diazepine-3-carboxamide, or a racemic mixture that is at least 80% S enantiomer.

13. The method of claim 1, wherein the subject is a human.

14. The method of claim 13, wherein the human subject in need is one at risk for cognitive impairment or neurocognitive decline associated with age or chronic stress, or one who is at risk of developing a neurological disease or disorder.

15. The method of claim 1, wherein the subject is a non-human subject, the method comprising administering to the non-human subject a composition suitable for veterinary use comprising an alpha5-GABAA receptor agonist.

* * * * *